United States Patent
Kobayashi et al.

(10) Patent No.: US 9,017,708 B2
(45) Date of Patent: Apr. 28, 2015

(54) MIXED ANTIBACTERIAL GLASS

(75) Inventors: Yoshinao Kobayashi, Tokyo (JP);
Takashi Fushimi, Osaka (JP); Noriyuki Nishiyama, Tokyo (JP); Satoshi Niigawa, Aichi (JP)

(73) Assignee: Koa Glass Co., Ltd., Tokyo (JP)

(*) Notice: Subject to any disclaimer, the term of this patent is extended or adjusted under 35 U.S.C. 154(b) by 330 days.

(21) Appl. No.: 12/998,497

(22) PCT Filed: Nov. 10, 2010

(86) PCT No.: PCT/JP2010/070027
§ 371 (c)(1),
(2), (4) Date: Apr. 27, 2011

(87) PCT Pub. No.: WO2011/148528
PCT Pub. Date: Dec. 1, 2011

(65) Prior Publication Data
US 2012/0015018 A1  Jan. 19, 2012

(30) Foreign Application Priority Data

May 27, 2010  (JP) ................. 2010-121301

(51) Int. Cl.
| | |
|---|---|
| *A01N 25/08* | (2006.01) |
| *A01N 59/16* | (2006.01) |
| *F24F 13/22* | (2006.01) |
| *C02F 1/50* | (2006.01) |
| *C03C 4/00* | (2006.01) |
| *C03C 12/00* | (2006.01) |
| *A61L 2/23* | (2006.01) |
| *C02F 103/02* | (2006.01) |

(52) U.S. Cl.
CPC ............ *F24F 13/222* (2013.01); *A01N 59/16* (2013.01); *A61L 2/23* (2013.01); *C02F 1/505* (2013.01); *C02F 2103/023* (2013.01); *C02F 2209/06* (2013.01); *C03C 4/0035* (2013.01); *C03C 12/00* (2013.01); *C03C 2204/02* (2013.01); *F24F 2013/227* (2013.01)

(58) Field of Classification Search
None
See application file for complete search history.

(56) References Cited

U.S. PATENT DOCUMENTS

2006/0142413 A1* 6/2006 Zimmer et al. ............... 523/122
2006/0166806 A1  7/2006 Fechner et al.

FOREIGN PATENT DOCUMENTS

| | | |
|---|---|---|
| JP | 01-313531 | 12/1989 |
| JP | 01317133 | 12/1989 |
| JP | 06-100329 | 4/1994 |
| JP | 10-72530 | 3/1998 |
| JP | 2001240426 | 4/2001 |
| JP | 2006-52918 | 2/2006 |
| JP | 2006-518696 A | 8/2006 |
| WO | 03082358 | 9/2003 |
| WO | 2005087675 | 9/2005 |
| WO | 2006/081800 | 2/2006 |
| WO | WO 2007/141978 A1 | 12/2007 |
| WO | WO 2007141978 A1 * | 12/2007 ............... C03C 4/00 |

OTHER PUBLICATIONS

English machine translation dated Jan. 13, 2011 of Kitamura et al., WO 2007/141978 A1, published Dec. 13, 2007.*

* cited by examiner

*Primary Examiner* — Michael B Pallay
(74) *Attorney, Agent, or Firm* — Carmody Torrance Sandak & Hennessey LLP

(57) ABSTRACT

A mixed antibacterial glass which stably controls the silver ion elution amount from the antibacterial glass into the drain water in an air conditioning system, thereby effectively preventing the occurrence of microorganisms in the drain water. The mixed antibacterial glass achieves antibacterial effect by releasing silver ions, and contains an antibacterial glass which shows alkalinity when dissolved, and another antibacterial glass which shows acidity when dissolved, the silver ion elution amounts from the antibacterial glasses showing alkalinity or acidity being within certain ranges as measured under certain conditions, the compounding amount of the antibacterial glass showing alkalinity being from 10 to 100 parts by weight with reference to 100 parts by weight of the antibacterial glass showing acidity, and the total silver ion elution amount being within a certain range as measured under certain conditions.

6 Claims, 13 Drawing Sheets

PRIOR ART

PRIOR ART

PRIOR ART

MIXED ANTIBACTERIAL GLASS

CROSS REFERENCE TO RELATED APPLICATIONS

This application is a National Stage of International Application No. PCT/JP2010/70027, filed Nov. 10, 2010, the subject matter of which is herein incorporated by reference in its entirety.

BACKGROUND OF THE INVENTION

1. Field of the Invention

The present invention relates to a mixed antibacterial glass, and specifically to a mixed antibacterial glass which contains an alkaline antibacterial glass and an antibacterial acidic glass, and thus allows stable control of the silver ion elution amount.

2. Description of the Related Art

Air conditioners are typical air conditioning systems. In a common air conditioner, water is condensed in a heat exchanger, and the drain water is recovered in a drain pan, and intensively discharged outside through a drain pipe.

Particularly in a ceiling air conditioner for business use, the drain pan always keeps a certain amount of drain water, and is susceptible to the entry of airborne nutrients. Therefore, microorganisms such as bacteria and molds can rapidly grow to inhibit the discharge of the drain water.

In order to solve the problem, Patent Document 1 proposes a preventive method against the occurrence of microorganisms, including placing an antibacterial agent containing a water-soluble glass which can elute silver and/or copper ions in the drain pan of an air conditioner.

More specifically, the method preferably uses a water-soluble glass composed of 15 to 60% by weight of $SiO_2$; to 40% by weight of at least one selected from the group consisting of $Li_2O$, $Na_2O$, and $K_2O$; 0.1 to 5% by weight of $Ag_2O$ and/or CuO; 10 to 50% by weight of $P_2O_5$ and/or 5 to 50% by weight of $B_2O_3$; 0 to 20% by weight of at least one selected from the group consisting of MgO, CaO, SrO, and BaO; and 0 to 20% by weight of at least one selected from the group consisting of $Al_2O_3$, ZnO, $CeO_2$, $ZrO_2$, and $TiO_2$.

Patent Document 2 discloses an antibacterial phosphate glass with a silver ion elution amount of 0.5 ng/cm²/day or more when immersed in boiling water at 100° C. for 500 to 1000 hours, and then in water or an acid at 20° C. for 24 hours.

More specifically, the antibacterial phosphate glass includes glass components composed of $P_2O_5$: 56 to 59 mol %, MgO+CaO+ZnO: 33 to 38 mol %, and $Al_2O_3$: 6 to 8 mol %, and 0 to 5% by weight of $Ag_2O$, and has an average particle size of 2 to 20 μm.

Patent Document 3 discloses an antibacterial borosilicate glass which elutes silver ions.

More specifically, the antibacterial borosilicate glass includes 100 parts by weight of glass solid component composed of one or more network-forming oxides selected from $SiO_2$, $B_2O_3$, and $P_2O_5$, and one or more network-modifying oxide selected from $Na_2O$, $K_2O$, CaO, and ZnO, and 0.1 to 20 parts by weight of $Ag_2O$ as monovalent Ag.

PRIOR ART DOCUMENTS

Patent Document

[Patent Document 1] JP2006-52918A (claims)
[Patent Document 2] JP10-72530A (claims)
[Patent Document 3] JP1-313531A (claims)

SUMMARY OF THE INVENTION

However, in the preventive method against the occurrence of microorganisms described in Patent Document 1, there is no consideration for the relationship between the pH of the water-soluble glass (reciprocal common logarithm of the hydrogen ion concentration) and the silver ion elution amount, so that the stable control of the silver ion elution amount is difficult with an antibacterial phosphate glass containing a relatively large amount of $P_2O_5$.

More specifically, the phosphate component is eluted into the drain water together with silver ions upon the dissolution of the antibacterial phosphate glass, and thus the pH of the drain water tends to shift to the acidic range when the supply of condensed water for diluting the drain water is stopped, though the situation varies depending on the specific surface area of the antibacterial glass.

As a result, the shift of the pH of the drain water to the acidic range further accelerates the dissolution of the antibacterial phosphate glass, and thus the silver ion elution amount tends to be excessive.

Also the antibacterial phosphate glass described in Patent Document 2, as in the case with Patent Document 1, tends to elute an excessive amount of silver ions.

Also in the antibacterial borosilicate glass described in Patent Document 3, there is no consideration for the relationship between the pH of the water-soluble glass and the silver ion elution amount, so that the stable control of the silver ion elution amount is likely difficult.

More specifically, the antibacterial borosilicate glass described in Patent Document 3 contains relatively large amounts of alkaline components such as sodium, potassium, and lithium as the ingredients, and thus elutes alkali components together with silver ions into the drain water upon the dissolution of the antibacterial borosilicate glass. Therefore, the pH of the drain water tends to shift to the alkaline range when the supply of condensed water for diluting the drain water is stopped, though the situation varies depending on the specific surface area of the antibacterial glass.

As a result, the shift of the pH of the drain water to the alkaline range further accelerates the dissolution of the antibacterial borosilicate glass, and thus the silver ion elution amount tends to be excessive.

Furthermore, the antibacterial borosilicate glass described in Patent Document 3 increase the pH of the drain water, and thus hinders complicates the observance of water pollution standard related to the hydrogen ion concentration, and accelerates the deterioration of the drain pan or drain pump made of resin.

Accordingly, there is a need for an antibacterial glass which allows stable control of silver ion elution amount.

As a result of dedicated research by the inventors, they have found that the silver ion elution amount can be stably controlled by the interaction between an antibacterial glass which becomes alkaline when dissolved (hereinafter may be referred to as an antibacterial alkaline glass), and another antibacterial glass which becomes acidic when dissolved (hereinafter may be referred to as an antibacterial acidic glass), which are mixed so as to satisfy certain conditions.

More specifically, antibacterial alkaline and acidic glasses having certain silver ion elution amounts under certain conditions (hereinafter may be referred to as standard silver ion elution amounts) are mixed at a certain mixing ratio, wherein the standard silver ion elution amount from the mixed antibacterial glass (hereinafter may be referred to as the standard total silver ion elution amount) is limited within a certain range. As a result, the silver ion elution amount can be stably controlled over a long period of, for example, 200 days or longer.

More specifically, an object of the present invention is to provide a mixed antibacterial glass which stably controls the silver ion elution amount from the antibacterial glass into the drain water in an air conditioning system, thereby effectively preventing the occurrence of microorganisms in the drain water.

In order to solve the above problems, according to the present invention, there is provided a mixed antibacterial glass which achieves antibacterial effect by releasing silver ions, the mixed antibacterial glass including an antibacterial glass which shows alkalinity when dissolved, and another antibacterial glass which shows acidity when dissolved, the silver ion elution amount from the antibacterial glass showing alkalinity being from 0.005 to 1 mg/(g·1 liter, 24 Hrs, 30° C.) as measured under certain conditions, the silver ion elution amount from the antibacterial glass showing acidity being from 0.005 to 1 mg/(g·1 liter, 24 Hrs, 30° C.) as measured under certain conditions, the compounding amount (optionally referred to the addition amount or content) of the antibacterial glass showing alkalinity being from 10 to 120 parts by weight with reference to 100 parts by weight of the antibacterial glass showing acidity, and the total silver ion elution amount being from 0.01 to 5 mg/(g·1 liter, 24 Hrs, 30° C.) as measured under certain conditions.

More specifically, antibacterial alkaline and acidic glasses having certain standard silver ion elution amounts are mixed at a certain ratio to make a mixed antibacterial glass, such that these antibacterial glasses effectively interact with each other to stably control the total silver ion elution amount from the whole mixed antibacterial glass.

More specifically, the interaction can effectively reduce the pH dependence of the total silver ion elution amount from the whole mixed antibacterial glass.

In addition, the neutralization action of the antibacterial alkaline and acidic glasses can reduce the pH variation in the drain water.

As a result, the silver ion elution amount in the drain water can be stably controlled over a long period of, for example, 200 days or longer, and the occurrence of microorganisms in the drain water can be effectively prevented.

When the standard silver ion elution amount and the compounding amounts of the antibacterial glasses are within the range defined in the present invention, the mixed antibacterial glass is within the technical scope of the present invention, in spite of the time of measurement.

More specifically, the mixed antibacterial glass belonging to the technical scope of the present invention includes any mixed antibacterial glass whose initial structure is within the scope of the present invention, and other mixed antibacterial glass whose structure in use is within the scope of the present invention.

Further, to configure the mixed antibacterial glass of the present invention, a pH (hereinafter may be referred to as standard pH) measured under certain conditions is preferably 5 to 9.

According to the present embodiment, the total silver ion elution amount from the whole mixed antibacterial glass can be more stably controlled.

In addition, the control of the pH of the drain water to be discharged allows stable compliance with the water pollution standard related to the hydrogen ion concentration.

To configure the mixed antibacterial glass of the present invention, the antibacterial glass showing alkalinity is preferably an antibacterial borosilicate glass, and the antibacterial glass showing acidity is preferably an antibacterial phosphate glass.

According to the present embodiment, the standard silver ion elution amounts from the antibacterial alkaline and acidic glasses can be easily controlled to fall within certain ranges.

Accordingly, the total silver ion elution amount from the whole mixed antibacterial glass can be also easily controlled to fall within a certain range.

To configure the mixed antibacterial glass of the present invention, the specific surface area of the antibacterial glass showing alkalinity is preferably from 0.1 to 5 $cm^2/g$, and the specific surface area of the antibacterial glass showing acidity is preferably from 8 to 100 $cm^2/g$.

According to the present embodiment, the standard silver ion elution amounts from the antibacterial alkaline and acidic glasses can be more easily controlled to fall within certain ranges.

Accordingly, the total silver ion elution amount from the whole mixed antibacterial glass can be also more easily controlled to fall within a certain range.

To configure the mixed antibacterial glass of the present invention, the antibacterial glass showing alkalinity is preferably in the form of tablets having a maximum diameter of 5 to 20 mm.

According to the present embodiment, the specific surface area of the antibacterial alkaline glass is easily controlled, and the total silver ion elution amount from the whole antibacterial glass can be also more easily controlled.

To configure the mixed antibacterial glass of the present invention, the antibacterial glass showing acidity is preferably in the form of granules having an average particle size of 0.01 to 5 mm.

According to the present embodiment, the specific surface area of the antibacterial acidic glass is easily controlled, and the total silver ion elution amount from the whole antibacterial glass is also more easily controlled.

In addition, the mixed antibacterial glass can be packaged using a covering member at a high filling rate, which makes the mixed antibacterial glass more compact.

To configure the mixed antibacterial glass of the present invention, the mixed antibacterial glass preferably further includes a non-antibacterial glass and the compounding amount of the non-antibacterial glass is preferably from 5 to 100 parts by weight with reference to 100 parts by weight of the antibacterial glass showing acidity.

According to the present embodiment, binding between the antibacterial alkaline and acidic glasses is prevented, and the total silver ion elution amount from the whole antibacterial glass can be more stably maintained.

When the mixed antibacterial glass is packaged using a covering member, the addition of a certain amount of non-antibacterial glass decreases the weight variation as a whole. Accordingly, even if the mixed antibacterial glass loses its weight, the weight of the non-antibacterial glass can effectively prevent the escape of the package from the intended place.

To configure the mixed antibacterial glass of the present invention, the antibacterial glass showing alkalinity and the antibacterial glass showing acidity are preferably enclosed in a covering member having an opening for passing water.

According to the present embodiment, the mixed antibacterial glass can be easy to handle, and can be reliably and quickly placed in an intended location in an air conditioning system.

DETAILED DESCRIPTION OF THE EMBODIMENTS

Figure 1A:
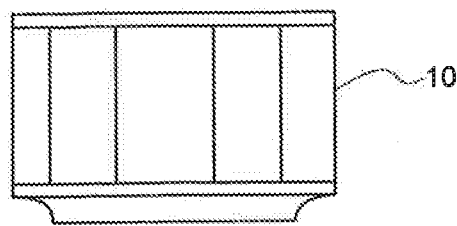
FIGS. 1A to 1C are schematic views of an air conditioning system.
Figure 1A:
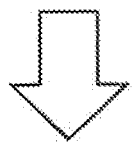
Figure 1B:
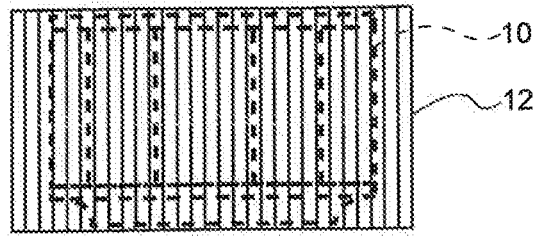
Figure 1B:
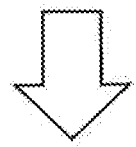
Figure 1C:
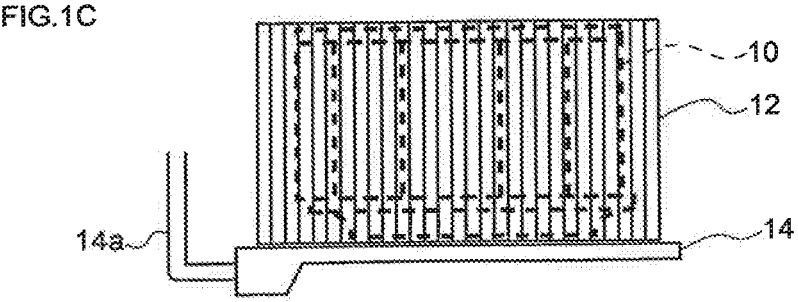

The mixed antibacterial glass of the present invention achieves antibacterial effect by releasing silver ions, and includes an antibacterial glass which shows alkalinity when dissolved, and another antibacterial glass which shows acidity when dissolved, the silver ion elution amount from the antibacterial glass showing alkalinity being from 0.005 to 1 mg/(g·1 liter, 24 Hrs, 30° C.) as measured under certain conditions, the silver ion elution amount from the antibacterial glass showing acidity being from 0.005 to 1 mg/(g·1 liter, 24 Hrs, 30° C.) as measured under certain conditions, the compounding amount of the antibacterial glass showing alkalinity being from 10 to 120 parts by weight with reference to 100 parts by weight of the antibacterial glass showing acidity, and the total silver ion elution amount being from 0.01 to 5 mg/(g·1 liter, 24 Hrs, 30° C.) as measured under certain conditions.

Embodiments of the mixed antibacterial glass will be specifically described below with the correlation between the pH and silver ion elution amount, antibacterial alkaline glass, and antibacterial acidic glass.

1. Applications

The type of the air conditioning system to which the present invention is applicable is not particularly limited as long as it includes a drain pan. Examples of the air conditioning system include gas heat pump air conditioners, electric heat pump air conditioners, and kerosene heat pump air conditioners.

Each of these air conditioning systems has a certain heat pump including a condenser, an expansion valve, an evaporator, and a compressor, and uses gas, electricity, or kerosene for driving the turbine in the compressor.

Of these air conditioning systems, specifically in air conditioning systems for business use, as shown in FIGS. 1A to 1C and FIGS. 2A to 2C, which are side views and plan views of an air conditioning system, respectively, a cooling medium is evaporated in an evaporator 12, thereby absorbing heat from the air in a blower fan housing 12' which is open at the upper and lower ends, and a blower fan 10 contained therein sends the cold air which has lost heat.

Consequently, the moisture in the air is condensed in large quantity on the surface of the evaporator 12. In order to recover the moisture, the air conditioning system for business use has a drain pan 14 at the bottom of the evaporator 12. The drain pan 14 has an air hole 10' for passing air from the blower fan 10 into the chamber.

In the drain pan 14, drain water is dropped into a drain water recovery section 18, and a pump 16 discharges the drain water outside.

Figure 2A:
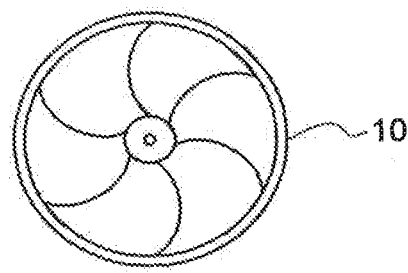
FIGS. 2A to 2C are another schematic views of an air conditioning system.
Figure 2B:
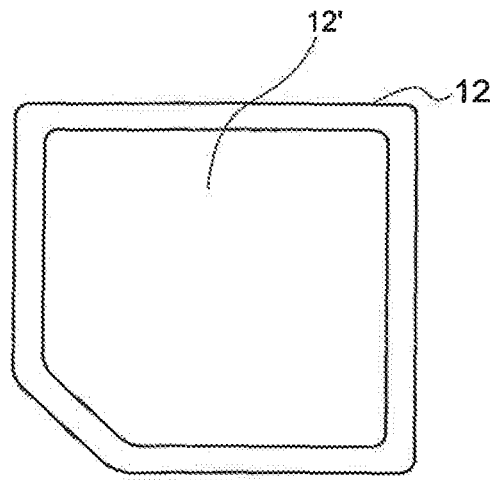
Figure 2C:
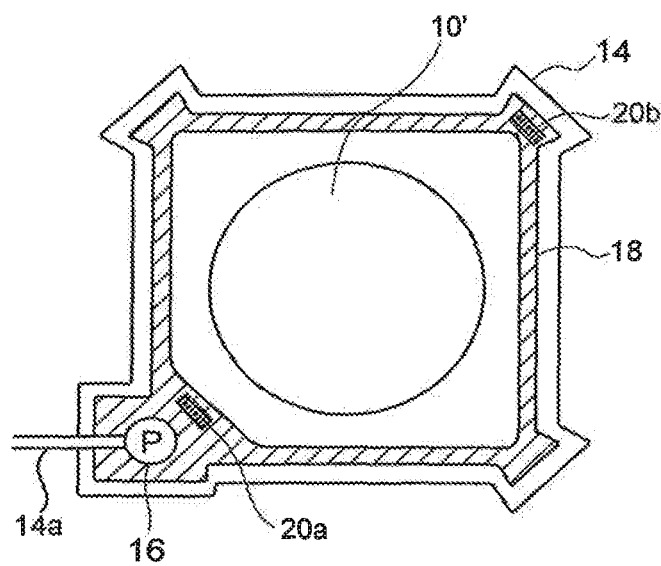

Therefore, as shown in FIG. 2C, the mixed antibacterial glasses 20(a) and 20(b) of the present invention are placed in the drain pan 14.

The mixed antibacterial glass 20 may be located at any place in the drain water recovery section 18, and may be near the pump 16 (20a) in which the drain water finally concentrates, other place (20b), or several places.

If a large amount of slime flows into the pump 16, the pump 16 may stop driving, and fail to discharge the drain water.

Accordingly, in order to prevent the occurrence of slime near the pump 16, it is particularly preferred that the mixed antibacterial glass 20 be arranged near the pump 16.

When the mixed antibacterial glass 20 is placed at a certain place, the mixed antibacterial glass 20 is preferably bound to, for example, a copper tube for passing the cooling medium.

This can prevent considerable movement of the mixed antibacterial glass 20 from the original place caused by the flow of the drain water.

The air conditioning system shown in FIGS. 1 and 2 is an example of the air conditioning system to which the mixed antibacterial glass of the present invention is applicable. The present invention is applicable to any air conditioning system as long as it has a drain pan.

Besides the above-described air conditioning systems, the mixed antibacterial glass of the present invention is also applicable to, for example, equipment keeping drain water, such as a boiler heat exchanger in a plant, and other equipment keeping water for a certain period, such as a water purifier, a washing machine, a humidifier, an air cleaner, and a nozzle cleaner of a warm-water cleaning toilet seat, and water storage tanks.

Other applications include condensed water storage tanks in drying type food garbage disposers.

2. Correlation Between pH and Silver Ion Elution Amount

In the present invention, antibacterial alkaline and acidic glasses are mixed to make a mixed antibacterial glass.

The reason is as follows. If an antibacterial alkaline or acidic glass is used alone, the pH dependence of the silver ion elution amount makes it difficult to stably control the silver ion elution amount.

On the other hand, through the use of the mixed antibacterial glass composed of antibacterial alkaline and acidic glasses, these antibacterial glasses effectively interact with each other to stably control the total silver ion elution amount from the whole antibacterial glass.

A more detailed explanation is given below with reference to FIGS. 3A to 3C.

Figure 3A:
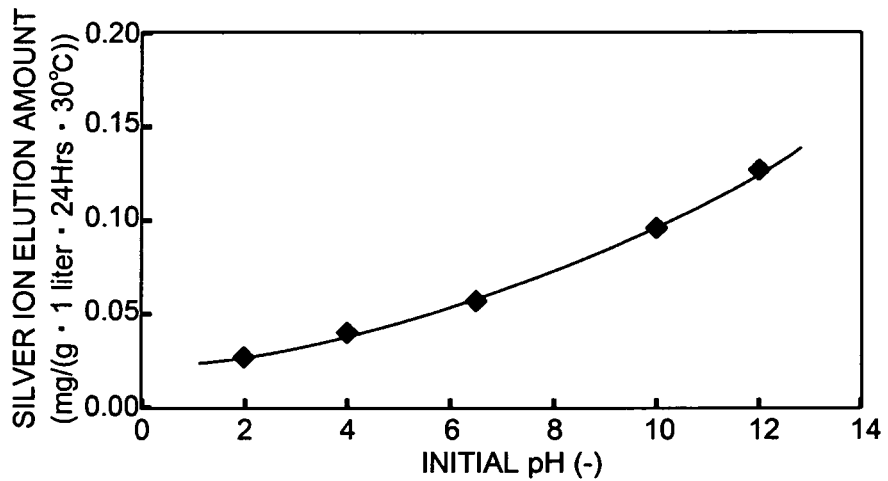
FIGS. 3A to 3C are graphs showing the relationship between the water pH and the silver ion elution amount.

FIG. 3A illustrates the correlation between the initial pH of water and the silver ion elution amount from an antibacterial borosilicate glass as an antibacterial alkaline glass immersed in the water alone.

FIG. 3A shows a characteristic curve wherein the initial pH of water (−) before immersing the antibacterial glass is taken on an axis of abscissas, and the silver ion elution amount (mg/(g·1 liter, 24 Hrs, 30° C.)) is taken on an axis of ordinates.

The antibacterial borosilicate glass was equivalent to that in Comparative Example 4.

The control of the initial pH of water to an acidic range used phosphoric acid or the combination of phosphoric acid and nitric acid. The control to an alkaline range used potassium hydroxide. The control of the pH was carried out in the same manner as in FIGS. 3B and 3C and the examples which will be described later.

The standard silver ion elution amount in the present invention means the silver ion elution amount measured as follows.

30 g of the antibacterial glass to be studied is immersed in 1 liter of purified water (30° C., pH 6.5) in a closed system for 24 hours with the temperature maintained.

Subsequently, the silver ion elute is filtrated through filter paper (5C) to make a measurement sample, and the silver ion concentration in the measurement sample is measured using an analytical instrument for measuring the silver ion concentration, such as a silver ion meter, an atomic absorption analyzer, or an ICP-MS analyzer, thereby calculating the silver ion elution amount (mg/(g·1 liter, 24 Hrs, 30° C.)).

In the preparation of the characteristic curves shown in FIG. 3A and others, the silver ion elution amounts at different pHs were measured and calculated under the same conditions as those for the standard silver ion elution amount, except that the initial pH of water before immersing the antibacterial glass was changed.

The "mg" as the numerator of the unit of the silver ion elution amount means the weight of silver ions, and the "g" as the denominator means the weight of the antibacterial glass.

The characteristic curve indicates that the silver ion elution amount increases as the increase in pH.

Accordingly, when an antibacterial borosilicate glass as an antibacterial alkaline glass is used alone in neutral drain water, the silver ion elution amount tends to be insufficient. Once the pH of the drain water is shifted to the alkaline range upon dissolution of the antibacterial glass, the silver ion elution amount tends to be excessive and cannot be stably controlled.

Depending on the composition of the antibacterial alkaline glass, the silver ion elution amount may excessively decrease as the pH of the drain water shifts to the alkaline range.

Also in this case, the use of the antibacterial alkaline glass alone makes it impossible to stably control the silver ion elution amount.

Figure 3B:
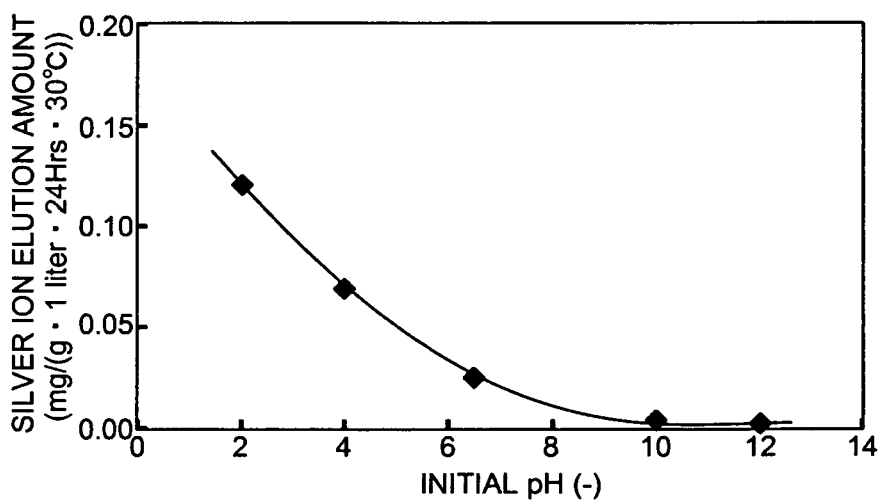

FIG. 3B illustrates the correlation between the initial pH and silver ion elution amount in the water in which the antibacterial phosphate glass as an antibacterial acidic glass was immersed alone.

FIG. 3B shows a characteristic curve wherein the initial pH (–) of water before immersing the antibacterial glass is taken on an axis of abscissas, and the silver ion elution amount (mg/(g·1 liter, 24 Hrs, 30° C.)) is taken on an axis of ordinates.

The antibacterial phosphate glass was equivalent to that in Comparative Example 1.

The characteristic curve indicates that the silver ion elution amount increases as the decrease in pH.

Accordingly, when an antibacterial phosphate glass as an antibacterial acidic glass is used alone in neutral drain water, the silver ion elution amount tends to be insufficient. Once the pH of the drain water is shifted to the acidic range by dissolution of the antibacterial glass, the silver ion elution amount tends to be excessive and cannot be stably controlled.

Figure 3C:
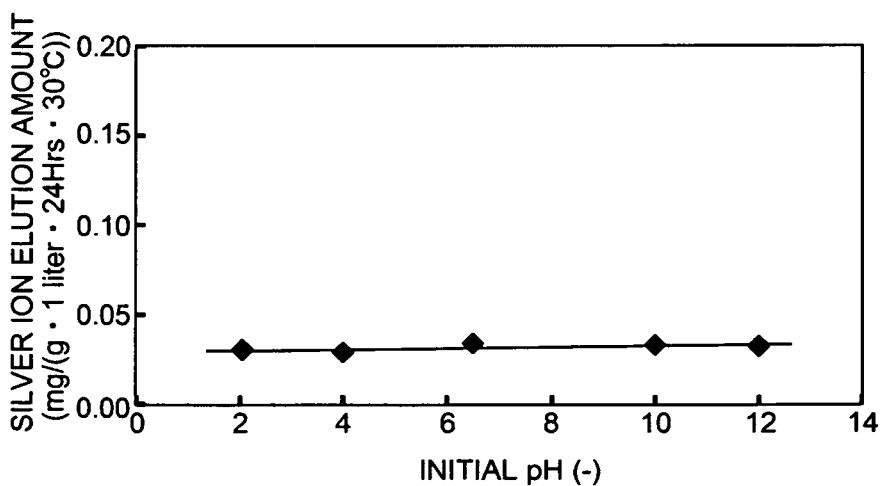

FIG. 3C illustrates the correlation between the initial pH and silver ion elution amount in the water in which the antibacterial borosilicate glass as an antibacterial alkaline glass and the antibacterial phosphate glass as an antibacterial acidic glass were immersed in combination.

FIG. 3C shows a characteristic curve wherein the initial pH (–) of water before immersing the antibacterial glass is taken on an axis of abscissas, and the silver ion elution amount (mg/(g·1 liter, 24 Hrs, 30° C.)) is taken on an axis of ordinates.

The mixed antibacterial glass was equivalent to that in Example 4.

The characteristic curve indicates that the silver ion elution amount is kept at a certain level irrespective of the pH variation.

The profile of the characteristic curve in FIG. 3C is markedly different from the simple sum of the characteristic curves in FIGS. 3A and 3B. The fact suggests that there is some interaction between the antibacterial alkaline and acidic glasses.

The gradient of the characteristic curve is relatively gentle, suggesting that the interaction effectively reduces the pH dependence of the silver ion elution amount in comparison with the cases using the antibacterial alkaline or acidic glass alone.

Accordingly, the combined use of the antibacterial alkaline and acidic glasses effectively reduces the pH dependence of the silver ion elution amount, and stably controls the silver ion elution amount in the drain water, and effectively prevents the occurrence of microorganisms in the drain water.

3. Antibacterial Alkaline Glass
(1) Standard Silver Ion Elution Amount

In the present invention, the standard silver ion elution amount from the antibacterial alkaline glass is from 0.005 to 1 mg/(g·1 liter, 24 Hrs, 30° C.).

The reason is as follows. When the silver ion elution amount from the antibacterial alkaline glass is within the above-described range, the total silver ion elution amount from the whole mixed antibacterial glass is readily and stably controlled to fall within a certain range, in combination with the standard silver ion elution amount from the antibacterial acidic glass and the proportions of the antibacterial glasses.

As a result, the silver ion elution amount in the drain water is stably controlled over a long period of, for example, 200 days or longer.

More specifically, when the standard silver ion elution amount from the antibacterial alkaline glass is less than 0.005 mg/(g·1 liter, 24 Hrs, 30° C.), the dissolution rate of the antibacterial alkaline glass decreases, and thus the total silver ion elution amount from the whole mixed antibacterial glass may be insufficient, the pH of the drain water may be too low, and the interaction with the antibacterial acidic glass may be insufficient.

On the other hand, if the standard silver ion elution amount from the antibacterial alkaline glass is more than 1 mg/(g·1 liter, 24 Hrs, 30° C.), the dissolution rate of the antibacterial alkaline glass increases, the total silver ion elution amount from the whole mixed antibacterial glass may be excessive, or the pH of the drain water may be too high.

Accordingly, the silver ion elution amount from the antibacterial alkaline glass is more preferably from 0.01 to 0.5 mg/(g·1 liter, 24 Hrs, 30° C.), and even more preferably from 0.1 to 0.3 mg/(g·1 liter, 24 Hrs, 30° C.).

Subsequently, the definition of the standard silver ion elution amount is more specifically described with reference to FIG. 4.

Figure 4:
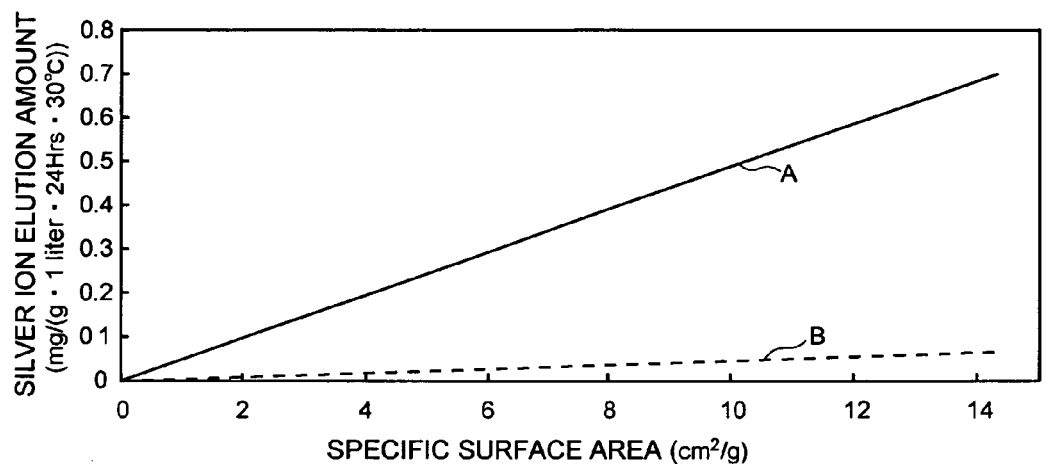
FIG. 4 is a graph showing the relationship between the specific surface area of and the silver ion elution amounts from the antibacterial alkaline and acidic glasses.

FIG. 4 shows characteristic curves A and B, wherein the specific surface area ($cm^2/g$) of the antibacterial glass is taken on an axis of abscissa, and the standard silver ion elution amount (mg/g·1 liter, 24 Hrs, 30° C.) is taken on an axis of ordinates.

The characteristic curve A represents a case using an antibacterial borosilicate glass (corresponding to Comparative Example 2), which is an antibacterial alkaline glass, as the antibacterial glass, and the characteristic curve B represents a case using an antibacterial phosphate glass (corresponding to Comparative Example 1), which is an antibacterial acidic glass, as the antibacterial glass.

These characteristic curves A and B indicate that the specific surface area is proportional to the standard silver ion elution amount in these antibacterial glasses.

On the other hand, the gradient of the characteristic curves are markedly different; the gradient of the characteristic curve A is about 10 times greater than that of the characteristic curve B.

The fact indicates that, when the specific surface area is equal, the antibacterial borosilicate glass (corresponding to Comparative Example 2), which is an antibacterial alkaline glass, elutes about 10 times more silver ions than the antibacterial phosphate glass (corresponding to Comparative Example 1), which is an antibacterial acidic glass.

The standard silver ion elution amount directly depends on the degree of dissolution of the antibacterial glass.

Therefore, the standard silver ion elution amount is useful as an index for evaluating the dissolution rate of the antibacterial glass, depending on the concentration of silver contained in the antibacterial glass.

Accordingly, from such viewpoint, the characteristic curves A and B indicate that, when the specific surface area is equal, the antibacterial borosilicate glass (corresponding to Comparative Example 2), which is an antibacterial alkaline glass, dissolves about 10 times faster than the antibacterial phosphate glass (corresponding to Comparative Example 1), which is an antibacterial acidic glass.

The present invention defines the standard silver ion elution amounts of the antibacterial glasses, thereby indirectly defining the dissolution rates of the antibacterial glasses.

As a result, the interaction between the antibacterial alkaline and acidic glasses is effectively achieved, whereby the variation in the silver ion elution amount due to the pH dependence is prevented, and thus the total silver ion elution amount from the whole mixed antibacterial glass is more stably controlled.

(2) Type 1

The type of the antibacterial alkaline glass is not particularly limited, but, for example, preferably an antibacterial borosilicate glass having the composition described below.

The reason is as follows. The use of the antibacterial borosilicate glass facilitates the control of the silver ion elution amount from the antibacterial alkaline glass, and also facilitates the control of the total silver ion elution amount in the drain water.

More specifically, the antibacterial alkaline glass contains $B_2O_3$, $SiO_2$, $Ag_2O$, and an alkali metal oxide, wherein, with reference to the total amount, the addition amount of $B_2O_3$ is from 30 to 60% by weight, $SiO_2$ is from 30 to 60% by weight, $Ag_2O$ is from 2 to 5% by weight, the alkali metal oxide is from 5 to 20% by weight, $Al_2O_3$ is from 0.1 to 2% by weight. When the total amount is less than 100% by weight, the balance is preferably filled with other glass component (for example, alkaline earth metal oxide, $CeO_2$, or $CoO$) in a proportion of 0.1 to 33% by weight.

In the composition of the antibacterial alkaline glass, $B_2O_3$ basically works as a network-forming oxide, and also contributes to the improvement of transparency and uniform emission of silver ions.

$SiO_2$ works as a network-forming oxide in the antibacterial glass, and prevents yellowing.

$Ag_2O$ is an essential component of the antibacterial glass, and elutes silver ions upon dissolution of the glass component, to achieve marked antibacterial activity over a long period of time.

An alkali metal oxides such as $Na_2O$ or $K_2O$ basically works as a network-modifying oxide, and controls the dissolution property of the antibacterial glass to reduce the water resistance of the antibacterial glass, and thus controls the silver ion elution amount from the antibacterial glass.

Further, an alkaline earth metal oxide such as MgO or CaO works as a network-modifying oxide, and also contributes to the improvement of the transparency and control of the melting temperature of the antibacterial glass like an alkali metal oxide.

Other additives such as $CeO_2$ or $Al_2O_3$ may be added to improve discoloration by electron beams, transparency, or mechanical strength.

(3) Type 2

The antibacterial alkaline glass contains an inorganic coloring agent, the addition amount of the inorganic coloring agent being preferably from 0.001 to 0.5% by weight, with reference to the total amount.

The reason is as follows. The addition of the inorganic coloring agent in a certain amount prevents discoloration of the antibacterial alkaline glass, and makes visible the disappearance of the antibacterial alkaline glass.

Accordingly, the initial appearance and discrimination are kept over a long period while antibacterial effect is kept at a certain level. More specifically, the inorganic coloring agent makes the silver ions to effectively prevent discoloration, and makes the antibacterial alkaline glass readily visible from the outside even when it is enclosed in a covering member. As a result, the refilling or replacement timing can be accurately estimated.

Accordingly, the addition amount of the inorganic coloring agent in the antibacterial alkaline glass is more preferably from 0.003 to 0.1% by weight, and even more preferably from 0.005 to 0.05% by weight with reference to the total amount.

When establishing the addition amount of the inorganic coloring agent contained in the antibacterial alkaline glass, it is preferred that the amount of the silver oxide be taken into consideration.

More specifically, when the addition amounts of the inorganic coloring agent and silver oxide contained in the antibacterial alkaline glass are C1 and C2, respectively, the C1/C2 ratio is preferably from 0.01 to 3.

The reason is as follows. When the addition amount of the inorganic coloring agent is established in consideration of the addition amount of silver oxide, the initial appearance and discrimination are kept without hindering the achievement of certain antibacterial effect. More specifically, if the C1/C2 ratio is less than 0.01, discoloration may be insufficiently prevented. On the other hand, if the C1/C2 ratio is more than 3, antibacterial effect may be poorly achieved.

Accordingly, the C1/C2 ratio is more preferably from 0.01 to 2, and even more preferably from 0.05 to 1.

The inorganic coloring agent is not particularly limited as to its type, and examples of the inorganic coloring agent which readily develop their colors in an oxidizing atmosphere include cobalt oxide (CoO), copper oxide (CuO), chromium oxide ($Cr_2O_3$), nickel oxide (NiO), manganese oxide ($MnO_2$), neodymium oxide ($Nd_2O_3$), erbium oxide ($Er_2O_3$), and cerium oxide ($CeO_2$), and combinations of two or more thereof.

For example, cobalt oxide (CoO) develop a markedly vivid blue color even in a very small amount, for example, 0.005% by weight, whereby the initial appearance and discrimination are kept without hindering the achievement of certain antibacterial effect.

(4) Specific Surface Area

The specific surface area of the antibacterial alkaline glass is preferably from 0.1 to 5 cm$^2$/g.

The reason is as follows. When the specific surface area of the antibacterial alkaline glass is within the above-described range, the standard silver ion elution amount from the antibacterial alkaline glass is more easily controlled to fall within a certain range.

More specifically, when the specific surface area of the antibacterial alkaline glass is less than 0.1 cm$^2$/g, the dissolution rate of the antibacterial alkaline glass decreases, whereby the total silver ion elution amount from the whole mixed antibacterial glass may be insufficient, the pH of the drain water may be too low, and the interaction with the antibacterial acidic glass may be insufficient.

On the other hand, if the specific surface area of the antibacterial alkaline glass is more than 5 cm$^2$/g, the dissolution rate of the antibacterial alkaline glass increases, and thus the total silver ion elution amount from the whole mixed antibacterial glass may be excessive, and the pH of the drain water may be too high.

Accordingly, the specific surface area of the antibacterial alkaline glass is more preferably from 1 to 4.5 cm$^2$/g, and even more preferably from 2 to 4 cm$^2$/g.

The specific surface area of the antibacterial glass may be calculated directly from the surface area and weight.

If the direct surface area cannot be directly measured, the specific surface area may be indirectly calculated from the ratio of the silver ion elution amount of the glass to the silver ion elution amount of another antibacterial glass having the same composition and a known specific surface area.

(5) Form

The antibacterial alkaline glass is not particularly limited as to its form, but is preferably in the form of tablets.

The reason is as follows. When the antibacterial alkaline glass is in the above-described form, the specific surface area of the antibacterial alkaline glass is easily controlled, and the silver ion elution amount in the drain water is more easily controlled.

In addition, when the antibacterial alkaline glass is in the form of tablets, it can prevent the aggregation of the antibacterial acidic glass, which is in a form likely to cause aggregation.

Figure 5:
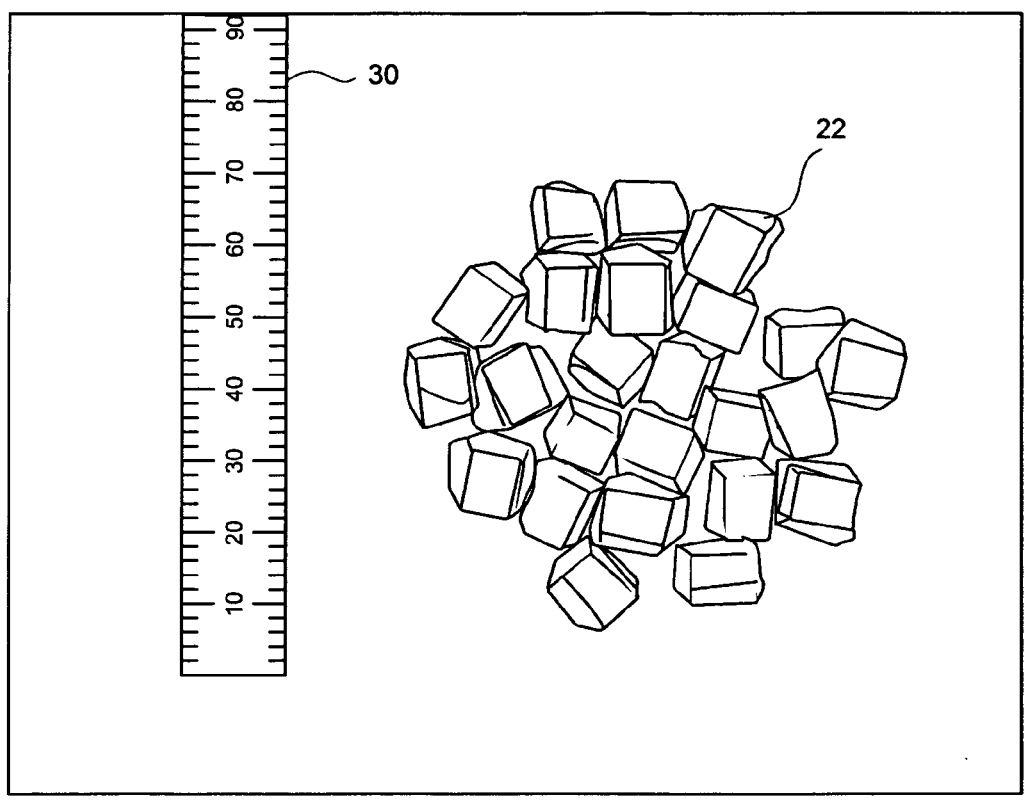
FIG. 5 illustrates the form of an antibacterial alkaline glass.

A specific example is an antibacterial alkaline glass 22 having the shape of a trapezoidal hexahedron shown in the illustration in FIG. 5. The antibacterial alkaline glass may be in the form of so-called tablets, such as rectangular parallelepiped or cylindrical column.

When the photograph is used as it is, it may be obscure on the document because of the deterioration of the image quality, hence an illustration was used in place of the photograph. The same thing applies to the illustrations in FIGS. 6, 8, 11, 12, and 13.

The antibacterial alkaline glass is preferably chamfered along the lines forming the glass.

The reason is as follows. When the antibacterial alkaline glass is in that form, the initial appearance and discrimination are kept over a prolonged period while antibacterial effect is kept at a certain level. In addition, the chamfered form improves the formability and grindability.

The antibacterial alkaline glass in the chamfered form facilitates the handling and replacement, and effectively prevents spill or crushing of the glass caused by a relatively strong stream of water.

The maximum diameter of the antibacterial alkaline glass is preferably from 5 to 20 mm. The maximum diameter of the antibacterial alkaline glass means the diameter of a circle circumscribing the antibacterial alkaline glass.

The reason is as follows. When the maximum diameter of the antibacterial alkaline glass is within the above-described range, the specific surface area of the antibacterial alkaline glass is more easily controlled, and the silver ion elution amount in the drain water is more easily controlled.

In addition, handling becomes easier, and the aggregation between the antibacterial glasses can be more effectively prevented.

If the maximum diameter is less than 5 mm, the glass put on a certain place may be washed away therefrom by water pressure after prolonged direct exposure to water, which may result in the fail to release a certain concentration of silver ions over a long period, and the aggregation of the glass tends to occur during storage.

On the other hand, if the maximum diameter is more than 20 mm, handling may be difficult, or stable production may be difficult.

Accordingly, the maximum diameter of the antibacterial alkaline glass is more preferably from 7 to 15 mm, and even more preferably from 9 to 12 mm.

The maximum diameter of the antibacterial glass can be easily measured using, for example, an optical microscope photograph or a vernier caliper.

The surface area of one piece of the antibacterial alkaline glass is preferably from 1 to 10 cm$^2$.

The reason is as follows. If the surface area is less than 1 cm$^2$, the specific surface area of the antibacterial alkaline glass may be excessively large, or the glass tends to cause aggregation.

On the other hand, if the surface area is more than 10 cm$^2$, the specific surface area of the antibacterial alkaline glass may be excessively small.

Accordingly, the surface area of one piece of the antibacterial alkaline glass is more preferably from 1.5 to 8 cm$^2$, and even more preferably from 2 to 5 cm$^2$.

(6) Standard pH

The standard pH of the antibacterial alkaline glass is preferably from 8 to 11.

The reason is as follows. If the standard pH of the antibacterial alkaline glass is outside the range of 8 to 11, the interaction with the antibacterial acidic glass may be insufficient, and the pH of the drain water may be excessively acidic or alkaline.

Accordingly, the pH of the antibacterial alkaline glass is preferably from 8.5 to 10.5, and more preferably from 9 to 10.

In the present invention, the standard pH means the pH measured under the same conditions as the above-described measurement conditions for the standard silver ion elution amount from the antibacterial glass.

(7) Compounding Amount

The compounding amount of the antibacterial alkaline glass is from 10 to 120 parts by weight with reference to 100 parts by weight of the below-described antibacterial acidic glass.

The reason is as follows. When the compounding amount of the antibacterial alkaline glass is within the above-described range, the silver ion elution amount in the drain water can be controlled to fall within a certain range, in combination with the standard silver ion elution amounts from the antibacterial alkaline and acidic glasses, or the dissolution rates.

In addition, the duration of the antibacterial effect in the drain water is easily controlled.

If the compounding amount of the antibacterial alkaline glass is less than 10 parts by weight, the total silver ion elution amount from the whole mixed antibacterial glass may be insufficient, the pH of the drain water may be too low, and the interaction with the antibacterial acidic glass may be insufficient.

On the other hand, if the compounding amount of the antibacterial alkaline glass is more than 120 parts by weight, the total silver ion elution amount from the whole mixed antibacterial glass may be excessive, and the pH of the drain water may be too high.

Accordingly, the compounding amount of the antibacterial alkaline glass is preferably from 20 to 80 parts by weight, and more preferably from 30 to 60 parts by weight with reference to antibacterial acidic glass 100 parts by weight.

4. Antibacterial Acidic Glass (1) Standard Silver Ion Elution Amount

In the present invention, the standard silver ion elution amount from the antibacterial acidic glass is from 0.005 to 1 mg/(g·1 liter, 24 Hrs, 30° C.).

The reason is as follows. When the silver ion elution amount from the antibacterial acidic glass is within the above-described range, the total silver ion elution amount from the whole mixed antibacterial glass can be readily and stably controlled to fall within a certain range, by controlling the standard silver ion elution amount from the antibacterial alkaline glass and the proportions of the antibacterial glasses.

As a result, the silver ion elution amount in the drain water is stably controlled over a long period of, for example, 200 days.

More specifically, when the standard silver ion elution amount from the antibacterial acidic glass is less than 0.005 mg/(g·1 liter, 24 Hrs, 30° C.), the dissolution rate of the antibacterial acidic glass decreases, and thus the total silver ion elution amount from the whole mixed antibacterial glass may be insufficient, the pH of the drain water may be too high, and the interaction with the antibacterial acidic glass may be insufficient.

On the other hand, if the standard silver ion elution amount from the antibacterial acidic glass is more than 1 mg/(g·1 liter, 24 Hrs, 30° C.), the dissolution rate of the antibacterial acidic glass increases, the total silver ion elution amount from the whole mixed antibacterial glass may be excessive, or the pH of the drain water may be too low.

Accordingly, the silver ion elution amount from the antibacterial acidic glass is more preferably from 0.01 to 0.5 mg/(g·1 liter, 24 Hrs, 30° C.), and even more preferably from 0.05 to 0.3 mg/(g·1 liter, 24 Hrs, 30° C.).

The standard silver ion elution amount means the silver ion elution amount measured under the same conditions as those for the antibacterial alkaline glass.

The standard silver ion elution amount from the antibacterial acidic glass is preferably established in consideration of the standard silver ion elution amount from the antibacterial alkaline glass.

The reason is as follows. When the standard silver ion elution amount from the antibacterial acidic glass is markedly different from the standard silver ion elution amount from the antibacterial alkaline glass, either of them may disappear, which makes it difficult to control the silver ion elution amount in the drain water.

Accordingly, specifically, the standard silver ion elution amount from the antibacterial acidic glass (A) is preferably from 0.1×B to 5×B, more preferably from 0.2×B to 3×B, and even more preferably from 0.3×B to 2×B with reference to the standard silver ion elution amount from the antibacterial alkaline glass (B).

(2) Type

The antibacterial acidic glass is not particularly limited as to its type, but is preferably, for example, an antibacterial phosphate glass having the following composition.

The reason is as follows. The use of the antibacterial phosphate glass facilitates the control of the silver ion elution amount from the antibacterial acidic glass, and also facilitates the control of the silver ion elution amount in the drain water.

In addition, the antibacterial phosphate glass having the composition is superior in processability, easy to be formed into granules having a certain particle size, and releases a certain amount of silver ions within a certain time.

Further, the antibacterial phosphate glass is less susceptible to corrosion in a melting furnace during production, and thus eases the production conditions and reduces the production cost to confer advantages in production.

The ingredients preferably include $Ag_2O$, CaO, $B_2O_3$, and $P_2O_5$, wherein, with reference to the total amount as 100% by weight, the content of $Ag_2O$ is from 2 to 5% by weight, CaO is from 10 to 30% by weight, $B_2O_3$ is from 1 to 15% by weight, and $P_2O_5$ is from 50 to 80% by weight. When the total amount is less than 100% by weight, the balance is preferably filled with other glass component (for example, alkali metal oxide, alkaline earth metal oxide, $CeO_2$, $Al_2O_3$, or CoO) in a proportion of 0.1 to 37% by weight.

In the composition of the antibacterial phosphate glass, $P_2O_5$ basically works as a network-forming oxide, and also contributes to the improvement of transparency and uniform release of silver ions.

$Ag_2O$ is an essential component of the antibacterial glass, and elutes silver ions upon dissolution of the glass component, to achieve marked antibacterial activity over a long period of time.

An alkali metal oxide such as $Na_2O$ or $K_2O$ fundamentally works as a network-modifying oxide, and also contributes to the improvement of the transparency and the control of the melting temperature of the antibacterial glass.

Further, an alkaline earth metal oxide such as MgO or CaO works as a network-modifying oxide, and improves the transparency and controls the melting temperature of the antibacterial glass like an alkali metal oxide.

Other additives such as $CeO_2$ or $Al_2O_3$ may be added to improve discoloration by electron beams, transparency, or mechanical strength.

The antibacterial acidic glass preferably contains an inorganic coloring agent such as cobalt oxide (CoO), the addition amount of the inorganic coloring agent being preferably from 0.001 to 0.5% by weight with reference to the total amount.

The reason is as follows. The addition of the inorganic coloring agent in a certain amount can prevent discoloration of the antibacterial glass, and makes visible the disappearance of the antibacterial acidic glass.

The antibacterial acidic glass is composed of $Ag_2O$, MgO, $K_2O$, ZnO, and $P_2O_5$, wherein, with reference to the total amount as 100% by weight, the content of $Ag_2O$ is more than 5% by weight to 10% by weight, MgO is from 3 to 10% by weight, $K_2O$ is from 5 to 20% by weight, ZnO is from 10 to 25% by weight, and $P_2O_5$ is from 55 to 75% by weight. When the total amount is less than 100% by weight, the balance is preferably filled with other glass component (for example, alkali metal oxide, alkaline earth metal oxide, $CeO_2$, $Al_2O_3$, or CoO) in a proportion of 0.1 to 37% by weight.

The reason is as follows. When the antibacterial acidic glass has the above-described composition, the antibacterial acidic glass contains a relatively large amount of $Ag_2O$, and stably increases the silver ion elution amount without collapsing the antibacterial acidic glass.

Accordingly, the antibacterial acidic glass having the composition easily fills the demand to increase the silver ion elution amount.

The improvement of the silver ion elution amount is demanded in, for example, an air conditioner wherein the copper tube in an evaporator is soaked in drain water. In this case, the silver ions eluted in the drain water with ionization adhere to the surface of the copper tube, and decrease the silver ion concentration in the drain water.

In other cases, for example, the space for placing the mixed antibacterial glass is limited due to the volume or form of the drain pan, so that the mixed antibacterial glass is required to be more compact.

Such demands can be easily filled by the antibacterial acidic glass having the above-described composition through the effective increase of the silver ion elution amount.

(3) Specific Surface Area

The specific surface area of the antibacterial acidic glass is preferably from 8 to 100 cm$^2$/g.

The reason is as follows. When the specific surface area of the antibacterial acidic glass is within the above range, the standard silver ion elution amount from the antibacterial acidic glass is more easily controlled to fall within a certain range.

If the specific surface area of the antibacterial acidic glass is less than 8 cm$^2$/g, the dissolution rate of the antibacterial acidic glass is excessively low, and thus the total silver ion elution amount from the whole mixed antibacterial glass may be insufficient, the pH of the drain water may be too high, and the interaction with the antibacterial alkaline glass may be insufficient.

On the other hand, if the specific surface area of the antibacterial acidic glass is more than 100 cm$^2$/g, the dissolution rate of the antibacterial acidic glass increases, so that the total silver ion elution amount from the whole mixed antibacterial glass may be excessive, and the pH of the drain water may be too low.

Accordingly, the specific surface area of the antibacterial acidic glass is more preferably from 9 to 50 cm$^2$/g, and even more preferably from 10 to 20 cm$^2$/g.

The specific surface area of the antibacterial glass may be calculated directly from the surface area and weight.

If the direct surface area cannot be directly measured, the specific surface area may be indirectly calculated from the ratio of the silver ion elution amount of the glass to the silver ion elution amount of another antibacterial glass having the same composition and a known specific surface area.

(4) Form

The antibacterial acidic glass is also not particularly limited as to its form, but is preferably in the form of granules.

The reason is as follows. When the antibacterial acidic glass is in the form of granules, the specific surface area of the antibacterial acidic glass is easily controlled, and the silver ion elution amount in the drain water can be more easily controlled.

More specifically, commonly, antibacterial acidic glass has a lower dissolution rate than antibacterial alkaline glass.

Accordingly, when the form is granular, the dissolution rate is improved, and a good balance is kept with the dissolution rate of the antibacterial alkaline glass.

Figure 6:
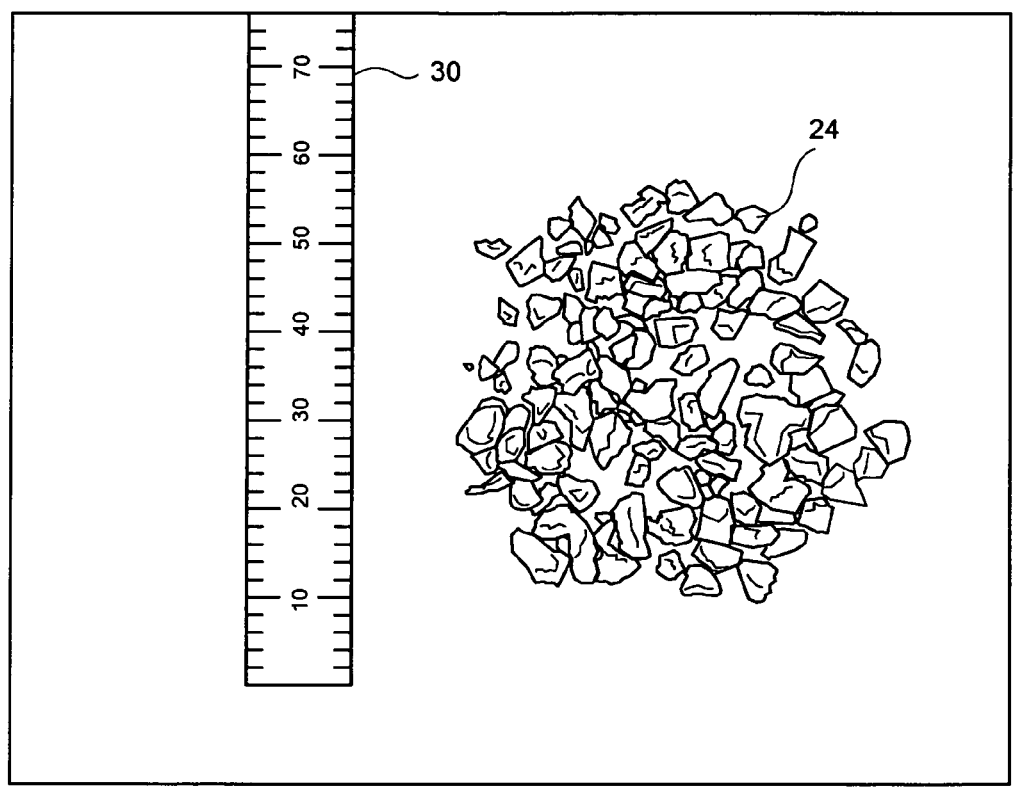
FIG. 6 illustrates the form of an acidic alkaline glass.

Among granules, an antibacterial acidic glass 24 in the form of crushed granules illustrated in FIG. 6 is particularly preferred, because it causes microcracks to further increases the dissolution rate.

Figure 7:
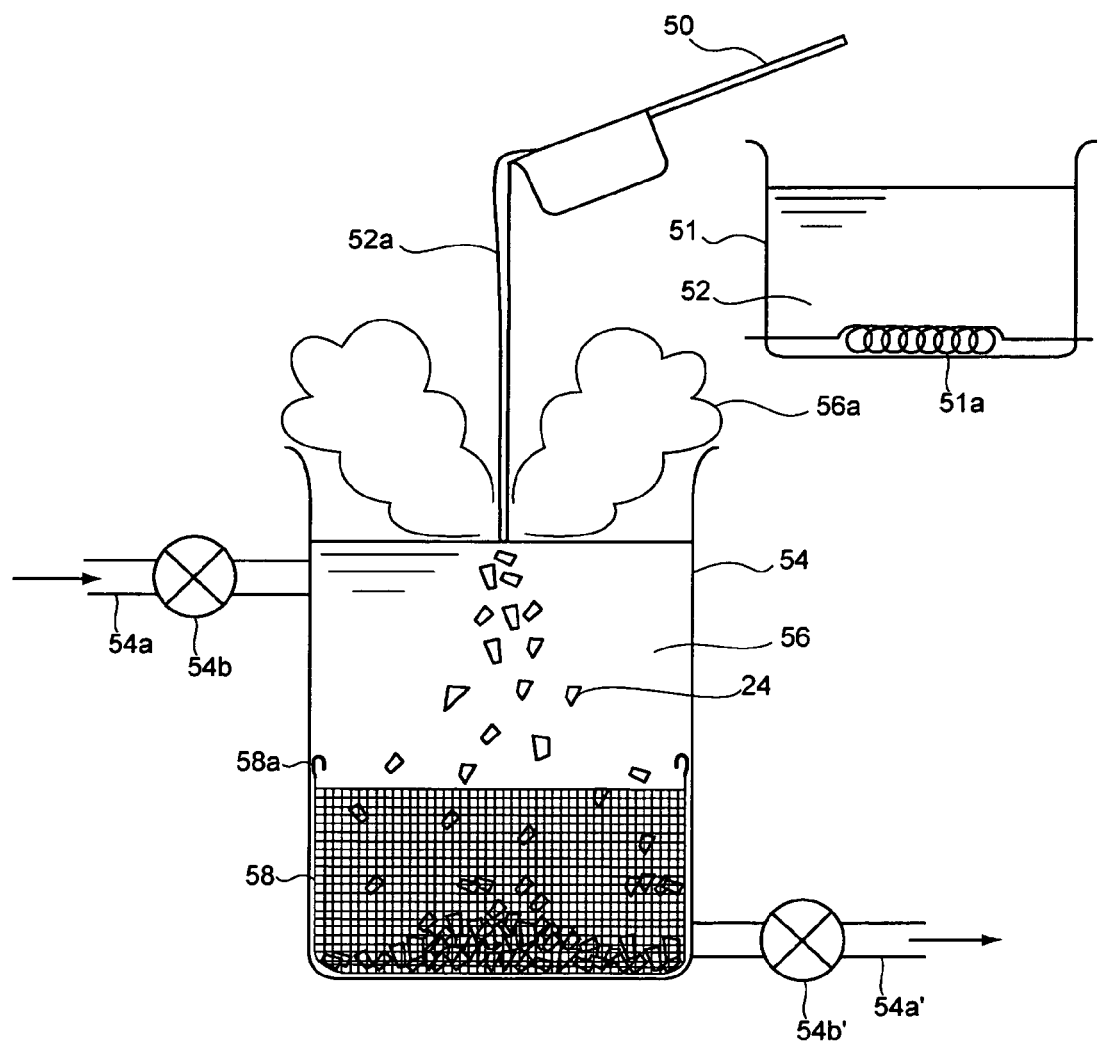
FIG. 7 illustrates the method for producing an antibacterial acidic glass.

The crushed granules are, as shown in FIG. 7, preferably obtained by so-called water granulation.

More specifically, molten glass 52 extracted from a glass melting furnace 51 with a ladle 50 is direct charged into water 56 in a water granulation vessel 54, thereby obtaining the crushed granules 24 of an antibacterial acidic glass.

The molten glass 52 is poured from the ladle 50 into the water 56 in the form of a continuous string molten glass 52a, thereby stably obtaining the crushed granules 24 having a desired particle size.

The temperature of the molten glass 52 is preferably from 600 to 1500° C., and more preferably 1000 to 1400° C.

The viscosity of the molten glass 52 is preferably from $1\times10^3$ to $1\times10^7$ Pa·sec (measured temperature: 25° C.), and more preferably from $1\times10^4$ to $1\times10^6$ Pa·sec.

The charging rate for the molten glass 52 is preferably from 0.1 to 10 liter/minute, and more preferably from 1 to 5 liter/minute.

The temperature of the water 56 in the water granulation vessel 54 is preferably from 0 to 70° C., and more preferably from 10 to 50° C.

The temperature of the water 56 in the water granulation vessel 54 is easily increased by pouring the molten glass 52a at high temperature. Therefore, as shown in FIG. 7, the water granulation vessel 54 is preferably provided with a water supply pipe 54a for appropriately adding water at a certain temperature and a valve 54b for controlling the water amount.

In this case, the water granulation vessel 54 is preferably provided with a drain pipe 54a' for draining the hot water 56 and a valve 54b' for controlling the drainage amount.

Further, as shown in FIG. 7, the water granulation vessel 54 preferably contains a recovery net 58 for easily recovering the crushed granules 24 obtained by water granulation.

The recovery net 58 preferably has one or more hooks 58a at the top, thereby facilitating the final recovery from the water granulation vessel 54.

The average particle size (number average particle size) of the antibacterial acidic glass is preferably from 0.01 to 5 mm.

The reason is as follows. When the average particle size of the antibacterial acidic glass is within the above-described range, the specific surface area of the antibacterial acidic glass can be more easily controlled, and the silver ion elution amount in the drain water can be more easily controlled.

If the average particle size is less than 0.01 mm, handleability may excessively deteriorate, or excessive aggregation may occur.

On the other hand, if the average particle size is more than 5 mm, the specific surface area decreases, and thus the dissolution rate may excessively decrease.

Accordingly, the average particle size of the antibacterial acidic glass is more preferably from 0.05 to 4 mm, and even more preferably from 0.1 to 3 mm.

The surface area of one piece of the antibacterial acidic glass is preferably from 0.00001 to 5 cm$^2$.

The reason is as follows. If the surface area is less than 0.00001 cm$^2$, the specific surface area of the antibacterial acidic glass may be excessively large, or aggregation tends to occur.

On the other hand, if the surface area is more than 5 cm$^2$, the specific surface area of the antibacterial acidic glass may be excessively small.

Accordingly, the surface area of one piece of the antibacterial acidic glass is more preferably from 0.0001 to 2 cm$^2$, and even more preferably from 0.001 to 1 cm$^2$.

(5) Standard pH

The standard pH of the antibacterial acidic glass is preferably from 2 to 6.

The reason is as follows. When the standard pH of the antibacterial acidic glass is outside the range of 2 to 6, the interaction with the antibacterial alkaline glass may not be effectively achieved, or the pH of the drain water may become excessively acidic or alkaline.

Accordingly, the standard pH of the antibacterial acidic glass is preferably from 2.5 to 5.5, and even more preferably from 3 to 5.

In the present invention, the standard pH means the pH measured under the same conditions for the above-described silver ion elution amount from the antibacterial alkaline glass.

5. Non-Antibacterial Glass

The mixed antibacterial glass preferably contains a certain amount of non-antibacterial glass.

The reason is as follows. The non-antibacterial glass prevents binding between the antibacterial alkaline and acidic glasses, and more facilitates the control of the total silver ion elution amount from the whole mixed antibacterial glass.

In addition, the certain amount of non-antibacterial glass decreases the variation in the total weight. As a result, even if the mixed antibacterial glass loses its weight, the weight of the non-antibacterial glass effectively can prevent escape of the package from the intended place.

(1) Type

The type of the non-antibacterial glass is not particularly limited as long as it is dissolved in water and will not elute silver ions. Preferred examples of the non-antibacterial glass include soda glass, borosilicate glass, lead glass (crystal glass), fused silica, aluminosilicate salt glass, and phosphate glass.

More specifically, the non-antibacterial glass is preferably composed mainly of soda glass, and 35 to 65% by weight of glass network components such as $SiO_2$, and 15 to 45% by weight of at least one glass network-modifier such as $Na_2O$, $K_2O$, $Li_2O$, $CaO$, $MgO$, $BaO$, $B_2O_3$, or $Al_2O_3$, with reference to the total amount.

It is also preferred that the non-antibacterial glass contains certain amounts of additives such as a reducing agent, an ultraviolet absorbing agent, and a coloring agent, which is different from those contained in the antibacterial alkaline or acidic glass.

(2) Form

Figure 8:
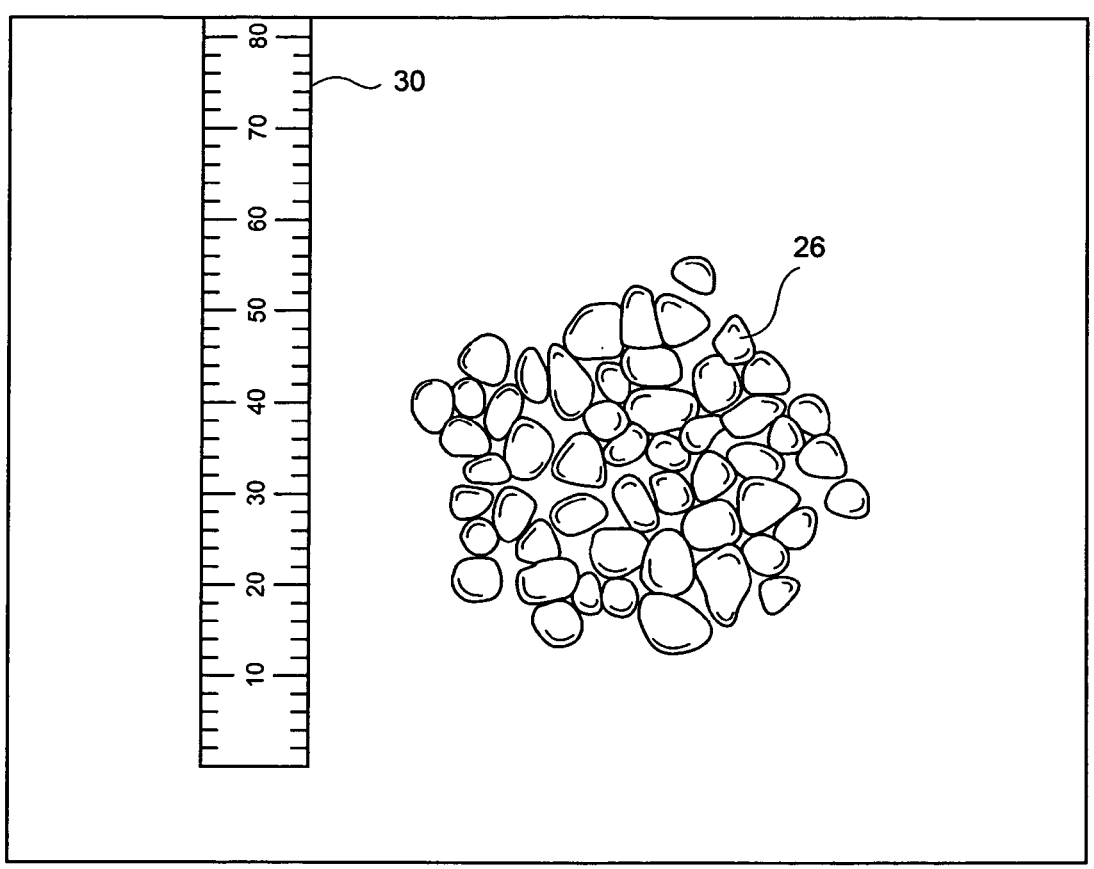
FIG. 8 illustrates the form of a non-antibacterial glass.

The non-antibacterial glass is not particularly limited as to its form. For example, a non-antibacterial glass 26 having different forms as illustrated in FIG. 8 is preferred.

The reason is as follows. The non-antibacterial glass 26 is readily molded, and effectively achieves weighing effect against the stream of water.

(3) Size

Regarding the size of the non-antibacterial glass, the maximum diameter is preferably from 3 to 30 mm.

The reason is as follows. The maximum diameter is substantially equal to those of the antibacterial glasses, whereby the non-antibacterial glass is uniformly mixed with the antibacterial glasses and will not be localized therein.

Accordingly, the maximum diameter of the non-antibacterial glass is more preferably from 5 to 20 mm, and even more preferably from 8 to 15 mm, thereby achieving antibacterial activity with a better balance, and facilitating the control of the total weight of the mixed antibacterial glass.

When the non-antibacterial glass is planar, the thickness of the non-antibacterial glass is preferably from 0.1 to 10 mm.

The reason is as follows. When the thickness of the non-antibacterial glass is less than 0.1 mm, the mechanical strength may markedly deteriorate, handling may be difficult, and stable production may be difficult. On the other hand, if the thickness of the non-antibacterial glass is more than 10 mm, handling may be difficult, and stable production may be difficult.

Accordingly, when the non-antibacterial glass is planar, the thickness of the non-antibacterial glass is preferably from 1 to 8 mm, and even more preferably from 2 to 5 mm.

(4) Compounding Amount

The compounding amount of the non-antibacterial glass is preferably from 5 to 100 parts by weight with reference to 100 parts by weight of the antibacterial acidic glass.

The reason is as follows. When the compounding amount of the non-antibacterial glass is within the above-described range, the mixed antibacterial glass achieves a certain level of antibacterial activity, and the total weight of the mixed antibacterial glass can be easily controlled. More specifically, when the compounding amount of the non-antibacterial glass is within the above-described range, the non-antibacterial glass is uniformly mixed with the antibacterial glasses and will not be localized therein, so that the antibacterial activity is uniformly achieved, and the total weight can be easily controlled.

Accordingly, in order to achieve antibacterial activity with a better balance, and to easily and accurately control the total weight of the mixed antibacterial glass, the compounding amount of the non-antibacterial glass is preferably from 8 to 80 parts by weight, more preferably from 10 to 50 parts by weight, and most preferably from 15 to 30 parts by weight with reference to 100 parts by weight of the antibacterial acidic glass.

6. Mixed Antibacterial Glass

(1) Standard Total Silver Ion Elution Amount

The standard total silver ion elution amount from the mixed antibacterial glass including at least of antibacterial alkaline and acidic glasses is from 0.01 to 5 mg/(g·1 liter, 24 Hrs, 30° C.).

The reason is as follows. If the standard total silver ion elution amount is less than 0.01 mg/(g·1 liter, 24 Hrs, 30° C.), the glass may fail to quickly release a certain concentration of silver ions upon direct contact with water to achieve certain antibacterial effect.

On the other hand, if the standard total silver ion elution amount is more than 5 mg/(g·1 liter, 24 Hrs, 30° C.), the release of a certain concentration of silver ions over a long period of time may be difficult, handling may be difficult, or stable production may be difficult.

Accordingly, the standard total silver ion elution amount from the mixed antibacterial glass is more preferably from 0.05 to 1 mg/(g·1 liter, 24 Hrs, 30° C.), and even more preferably from 0.1 to 0.2 mg/(g·1 liter, 24 Hrs, 30° C.).

The standard total silver ion elution amount from the mixed antibacterial glass means the silver ion elution amount measured under the same conditions as the above-described measurement conditions for the silver ion elution amount from the antibacterial alkaline glass.

(2) Standard pH

The standard pH of the mixed antibacterial glass is preferably from 5 to 9.

The reason is as follows. When the standard pH of the mixed antibacterial glass is within the above-described range, the silver ion elution amount in the drain water is stably controlled to fall within a certain range, in combination with the standard silver ion elution amounts and proportions of the antibacterial glasses.

If the standard pH of the mixed antibacterial glass is less than 5, the pH of the drain water is too low, the silver ion elution amount from the antibacterial glasses may be excessively low, which may result in intolerance to long-term use.

On the other hand, if the pH of the mixed antibacterial glass is more than 9, the pH of the drain water may be too high, the silver ion elution amounts from the antibacterial glasses may be excessively low, which may result in the fail to achieve sufficient antibacterial effect. Furthermore, it may difficult to comply with standards for water pollution related to the hydrogen ion concentration.

Accordingly, the standard pH of the mixed antibacterial glass is preferably from 6.0 to 8.4, and even more preferably from 6.2 to 8.2.

The standard pH of the antibacterial glass means the pH measured under the same conditions as those for the above-described measurement of the silver ion elution amount from the antibacterial alkaline glass.

(3) Addition Amount

The addition amount of the mixed antibacterial glass is not particularly limited, but preferably, for example, from 10 to 100 g, and more preferably from 20 to 80 g with reference to a drain pan which recovers and keeps up to 1 liter of drain water.

The reason is as follows. When the amount of the mixed antibacterial glass is within the above-described range, a service life of, for example, 200 days or longer can be ensured.

(4) Other Aspects

Even if the type (composition), specific surface area, form, and compounding amount of the antibacterial alkaline and acidic glasses are outside the above-described ranges, the total silver ion elution amount from the whole antibacterial glass can be stably controlled as long as the standard silver ion elution amount and the compounding amounts of the antibacterial glasses are within the range defined in the present invention.

More specifically, the standard silver ion elution amounts from the antibacterial glasses are controllable by changing the silver content and glass composition, or by changing the form and specific surface area.

As an example of other aspects, a mixed antibacterial glass composed of an antibacterial alkaline glass having a lower solubility than the above-described antibacterial alkaline glass is described below.

(4)-1 Antibacterial Alkaline Glass

A borosilicate glass as an antibacterial alkaline glass contains $B_2O_3$, $SiO_2$, $Ag_2O$, and an alkali metal oxide, wherein, with reference to the total amount, the addition amount of $B_2O_3$ is from 30 to 60% by weight, $SiO_2$ is from 30 to 60% by weight, $Ag_2O$ is from 2 to 5% by weight, the alkali metal oxide is from 5 to 20% by weight, $Al_2O_3$ is from 2 to 15% by weight. When the total amount is less than 100% by weight, the balance is preferably filled with other glass component (for example, alkali metal oxide, or $K_2O$) in a proportion of 0.1 to 33% by weight.

The borosilicate glass contains a greater addition amount of $Al_2O_3$, which form a stronger network than $B_2O_3$ or $SiO_2$, whereby the dissolution rate is decreased, and the silver ion elution amount is also decreased.

When the borosilicate glass of this type is used, the specific surface area is preferably from 8 to 100 $cm^2/g$, and more preferably from 10 to 20 $cm^2/g$, thereby achieving a certain standard silver ion elution amount.

In order to achieve the specific surface area, the borosilicate glass is preferably in the form of granules, and specifically in the form of crushed granules, as described in the section of the antibacterial acidic glass.

In this case, the average particle size of the borosilicate glass is preferably from 0.01 to 5 mm, and even more preferably from 0.1 to 3 mm.

The surface area of one piece of the borosilicate glass is preferably from 0.00001 to 5 $cm^2$, and more preferably from 0.001 to 1 $cm^2$.

According to the present embodiment, the antibacterial alkaline glass has a standard silver ion elution amount of 0.01 to 0.3 mg/(g·1 liter, 24 Hrs, 30° C.), more preferably from 0.05 to 0.1 mg/(g·1 liter, 24 Hrs, 30° C.).

The antibacterial alkaline glass has a standard pH of 8.5 to 10.5, more preferably from 9 to 10.

(4)-2 Antibacterial Acidic Glass

The antibacterial acidic glass to be mixed with the above-described antibacterial alkaline glass is preferably the same one as the above-described antibacterial phosphate glass.

The specific surface area is preferably from 0.1 to 5 $cm^2/g$, and more preferably from 2 to 4 $cm^2/g$, corresponding to that of the above-described antibacterial alkaline glass having a decreased dissolution rate.

In order to achieve the specific surface area, the antibacterial phosphate glass is preferably in the form of tablets.

In this case, the maximum diameter of the phosphate glass is preferably from 5 to 20 mm, and even more preferably from 9 to 12 mm.

Further, the surface area of one piece of the phosphate glass is preferably from 1 to 10 $cm^2$, and more preferably from 2 to 5 $cm^2$.

According to the present embodiment, the antibacterial alkaline glass has a standard silver ion elution amount of 0.01 to 0.2 mg/(g·1 liter, 24 Hrs, 30° C.), more preferably from 0.02 to 0.1 mg/(g·1 liter, 24 Hrs, 30° C.).

The antibacterial alkaline glass has a standard pH of 3 to 6.5, more preferably from 4 to 6.

7. Covering Member

Figure 9A:
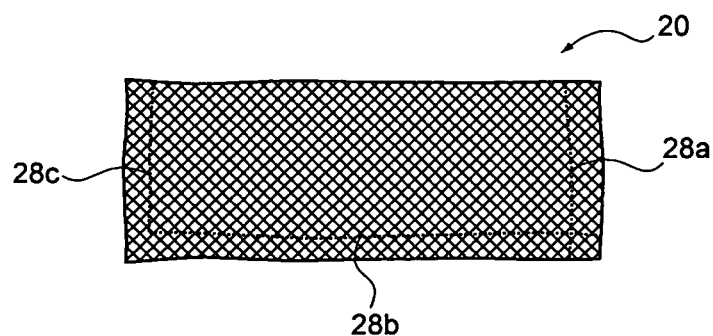
FIGS. 9A to 9C illustrate a covering member.
Figure 9B:
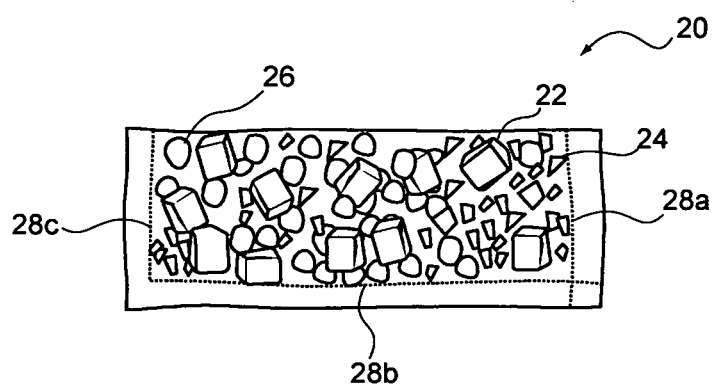
Figure 9C:
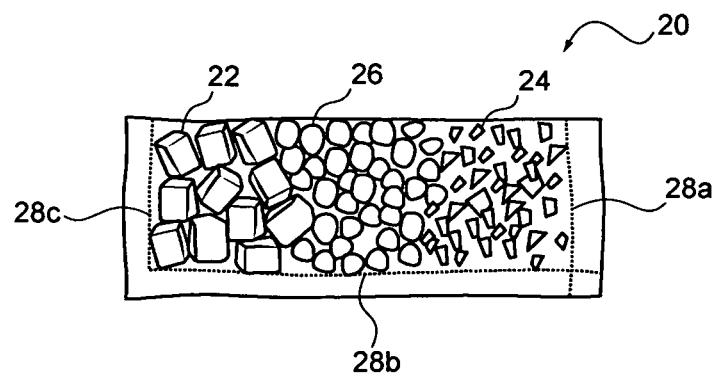

As shown in FIGS. 9A to 9C, the mixture of the antibacterial alkaline glass 22 and the antibacterial acidic glass 24 as a mixed antibacterial glass is preferably enclosed in a covering member 20 having an opening for passing water therethrough, to make a cartridge.

The reason is as follows. The covering member facilitates handling during storage, and prevents the aggregation of the mixed antibacterial glass. In addition, the covering member improves the usability, and prevents spill of the glass caused by a relatively strong stream of water. Further, the cartridge facilitates handling and replacement.

The covering member may be, for example, a mesh bag 20 as shown in FIG. 9A.

More specifically, for example, the bag is preferably made of a polypropylene mesh having openings of about 50 to 500 μm, and has a size of about 105×45×17 mm.

The bag preferably has seal portions 28b and 28c formed in advance, and another seal portion 28a formed after putting the mixed antibacterial glass in the bag.

The content of the mixed antibacterial glass is preferably from 10 to 100 g, and more preferably from 30 to 80 g.

The antibacterial glass contained in the cartridge is, for example, as shown in FIG. 9B, in the form of a mixture of the antibacterial alkaline glass 22, the antibacterial acidic glass 24, and optionally the non-antibacterial glass 26.

Alternatively, as shown in FIG. 9C, it is also preferred that the antibacterial alkaline glass 22, the antibacterial acidic glass 24, and the non-antibacterial glass 26 be put in the bag sequentially without mixing, thereby achieving a good production efficiency.

In the covering member 20 shown in FIGS. 9B to 9C, lines forming a mesh are not drawn, thereby illustrating the state of the mixed antibacterial glass enclosed in the covering member.

EXAMPLES

The present invention is further described below with reference to Examples. However, the following explanations are only exemplary, and the present invention will not limited thereto.

Example 1

1. Making of Mixed Antibacterial Glass (1) Making of Antibacterial Alkaline Glass
(1)-1 Melting Process As an antibacterial alkaline glass composition, a glass feedstock having the following composition was stirred until uniform using a universal mixer at a rotational speed of 250 rpm for 30 minutes.

$SiO_2$ 49.11% by weight
$Al_2O_3$ 0.76% by weight
$K_2O$ 8.98% by weight
$B_2O_3$ 37.90% by weight
$Ag_2O$ 2.99% by weight
$CoO$ 0.26% by weight Subsequently, using a glass melting furnace, the glass feedstock was heated at 1280° C. for 3.5 hours to make molten glass.

(1)-2 Molding Process

Figure 10A:
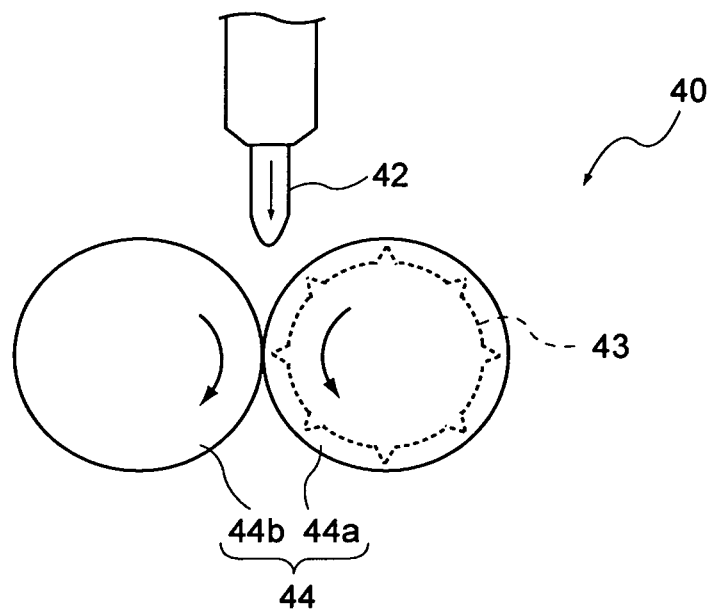
FIGS. 10A and 10B illustrate the method for producing an antibacterial alkaline glass.
Figure 10B:
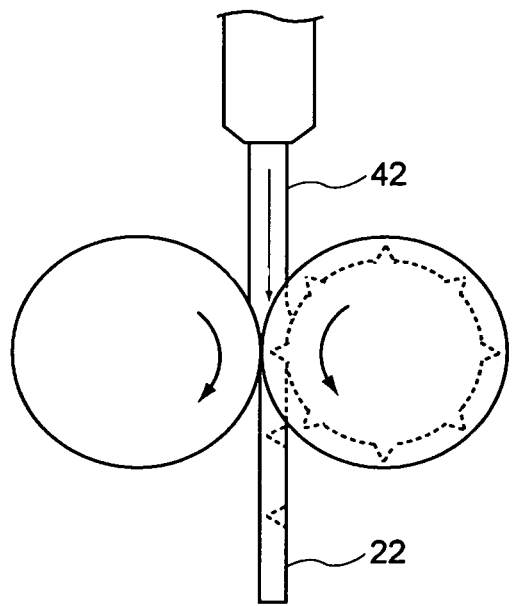

As shown in FIGS. 10A and 10B, molten glass 42 taken out from the glass melting furnace was introduced to a molding device 40, and thus the antibacterial alkaline glass 22 in the form of tablets as shown in FIG. 5 (maximum diameter: 10 mm, surface area of one piece: 2.5 cm$^2$) was molded.

(1)-3 Surface Grinding Process 500 g of the antibacterial alkaline glass in the form of tablets were changed into a vibration ball mill using no medium. Subsequently, 500 g of isopropyl alcohol or water was added, and the vibration ball mill was operated at room temperature for 30 minutes, thereby carrying out the surface grinding process including deburring process.

Minute irregularities were found before the surface grinding process, but the surface was smooth and glossy after the surface grinding process. The glass was used as the final antibacterial alkaline glass.

The specific surface area of the antibacterial alkaline glass was 3.75 cm$^2$/g.

(1)-4 Measurement of Standard Silver Ion Elution Amount

The standard silver ion elution amount of the antibacterial alkaline glass was measured.

More specifically, 30 g of the antibacterial alkaline glass was immersed in 1 liter of purified water (30° C., pH 6.5), and left standing in a closed system for 24 hours with the temperature maintained.

Subsequently, the silver ion elute was filtered through a filter paper (5C) to make a measurement sample, and then the silver ion concentration in the measurement sample was measured using a silver ion meter (manufactured by Toko Kagaku Kenkyusho, silver ion meter TiN-5104), and the standard silver ion elution amount from the antibacterial alkaline glass (mg/(g·1 liter, 24 Hrs, 30° C.)) was calculated. The obtained results are listed in Table 1.

(1)-5 Measurement of Standard pH

The standard pH of the antibacterial alkaline glass was measured.

More specifically, the pH of the measurement sample obtained under the same conditions as those for the measurement of the standard silver ion elution amount was measured using a pH test paper (manufactured by Toyo Roshi Kaisha, Ltd., ADVANTEC WHOLE RANGE pH 0 to 14). The obtained results are listed in Table 1.

(2) Making of Antibacterial Acidic Glass
(2)-1 Melting Process

As an antibacterial acidic glass composition, a glass feedstock having the following composition was stirred until uniform using a universal mixer at a rotational speed of 250 rpm for 30 minutes.

$P_2O_5$ 66.80% by weight
$CaO$ 21.99% by weight
$Al_2O_3$ 2.00% by weight
$Na_2O$ 0.60% by weight
$B_2O_3$ 5.00% by weight
$Ag_2O$ 3.04% by weight
$CeO_2$ 0.52% by weight
$CoO$ 0.05% by weight Subsequently, using a glass melting furnace, the glass feedstock was heated at 1280° C. for 3.5 hours to make molten glass.

(2)-2 Molding Process

As shown in FIG. 7, the molten glass 52 taken out from the glass melting furnace was dropped from the ladle 50 to the water 56 in the water granulation vessel 54, thereby achieving water granulation, and thus the antibacterial acidic glass 24 in the form of crushed granules having an average particle size of 2 mm as shown in FIG. 6 was obtained.

The temperature of the molten glass was 1280° C., the viscosity was 1×10$^5$ Pa·sec, the charging rate of the molten glass into water was 2 liter/minute, and the water temperature was 25° C.

The specific surface area of the antibacterial alkaline glass was 10.5 cm$^2$/g.

(2)-3 Measurement of Standard Silver Ion Elution Amount

The standard silver ion elution amount of the antibacterial acidic glass was measured.

The measurement was carried out in the same manner as the above-described measurement of the standard silver ion elution amount from the antibacterial alkaline glass. The obtained results are listed in Table 1.

(2)-4 Measurement of Standard pH

The standard pH of the antibacterial acidic glass was measured.

The measurement was carried out in the same manner as the above-described measurement of the standard pH of the antibacterial alkaline glass. The obtained results are listed in Table 1.

(3) Making of Non-Antibacterial Glass
(3)-1 Melting Process

As a non-antibacterial glass composition, a glass feedstock having the following composition is charged into a glass melting furnace.

$SiO_2$ 58.8% by weight
$Na_2O$ 27.0% by weight
$B_2O_3$ 10.0% by weight
$CaO$ 3.0% by weight
$K_2O$ 1.2% by weight Subsequently, the temperature of the glass melting furnace was set at 1350° C., and the glass feedstock was heated and molten for 10 hours.

(3)-2 Molding Process

Subsequently, the molten glass taken out from the glass melting furnace was once cooled and crushed to obtain cullet, and the cullet was heated in a rotary kiln, and edges were smoothened to mold the non-antibacterial glass 26 in different forms as shown in FIG. 8 (average particle size: 10 mm).

(4) Enclosure Process

Subsequently, as shown in FIG. 9C, 10 g of the antibacterial alkaline glass, 20 g of the antibacterial acidic glass, and 3 g of the non-antibacterial glass were enclosed in a polypropylene mesh bag (opening: 210 μm, external size: 105 mm×45 mm×about 17 mm) as the covering member 20, and thus the mixed antibacterial glass of Example 1 was obtained.

2. Evaluation of Mixed Antibacterial Glass (1) Evaluation of Total Silver Ion Elution Amount
(1)-1 Standard Total Silver Ion Elution Amount The standard total silver ion elution amount from the mixed antibacterial glass was evaluated.

The measurement was carried out in the same manner as the above-described measurement of the standard silver ion elution amount from the antibacterial alkaline glass. The obtained results are listed in Table 1.

(1)-2 Total Silver Ion Elution Amount Under Endurance Conditions

The total silver ion elution amount from the mixed antibacterial glass under endurance conditions was evaluated.

More specifically, the total amount of the mixed antibacterial glass (for example, 30 g in Example 1, and 70 g in Example 2) was immersed in 200 ml of purified water (30° C., pH 6.5) with the temperature maintained, and left standing for 14 days in an open system. After standing for 14 days, the purified water evaporated to 75 ml.

Subsequently, the silver ion elute was filtered through a filter paper (5C) to make a measurement sample, and then the silver ion concentration in the measurement sample was measured using a silver ion meter (manufactured by Toko Kagaku Kenkyusho, silver ion meter TiN-5104), and the standard silver ion elution amount from the antibacterial alkaline glass (mg/(g·1 liter, 24 Hrs, 30° C.)) under the endurance conditions was calculated. The obtained results are listed in Table 1.

When the total silver ion elution amount in 75 ml of purified water is converted into the total silver ion elution amount in 1 l of purified water, the difference of the amount of the purified water will have little influence on the absolute total silver ion elution amount (mg).

Accordingly, the total silver ion elution amount (mg/(g·1 liter·14 days·30° C.)) was calculated, on the assumption that the absolute total silver ion elution amount (mg) would not change regardless whether the amount of the purified water was 75 ml or 1 l.

With reference to the standard total silver ion elution amount, which is the total silver ion elution amount for 24 hours, the total silver ion elution amount under the endurance conditions, which is the total silver ion elution amount for 14 days, was, for example, not about 14 times, but as small as 2 to 4 times.

It has been empirically confirmed that the phenomenon is caused by the increase in the silver ion elution amount in the initial stage, which is due to that the antibacterial glass immersed in purified water in the initial stage usually has minute irregularities on its surface and thus has a large surface area, and often includes fine powder of the antibacterial glass generated during molding of the antibacterial glass.

(1)-3 Evaluation of pH Dependence

The pH dependence of the total silver ion elution amount from the mixed antibacterial glass was evaluated.

More specifically, the total silver ion elution amount was measured in the same manner as the measurement of the standard total silver ion elution amount, except that the pH of water before immersing the mixed antibacterial glass was changed to pH 4, 6.5, and 10, and the pH dependence of the total silver ion elution amount was evaluated. The obtained results are listed in Table 1.

(2) Evaluation of pH
(2)-1 Standard pH

The standard pH of the antibacterial glass was evaluated.

More specifically, the pH of the sample after a lapse of 24 hours, which had been obtained under the same conditions as the evaluation of the standard total silver ion elution amount, was measured. The obtained results are listed in Table 1.

(2)-2 pH Under Endurance Conditions

The pH of the antibacterial glass under endurance conditions was evaluated.

More specifically, the pH of the measurement sample after a lapse of 14 days, which had been obtained under the same conditions as those for the evaluation of the total silver ion elution amount under the endurance conditions, was measured. The obtained results are listed in Table 1.

(3) Evaluation of Antibacterial Activity 1

As an endurance test, the mixed antibacterial glass was subjected to continuous operation of an air conditioner, and the antibacterial activity was evaluated.

Figure 11:
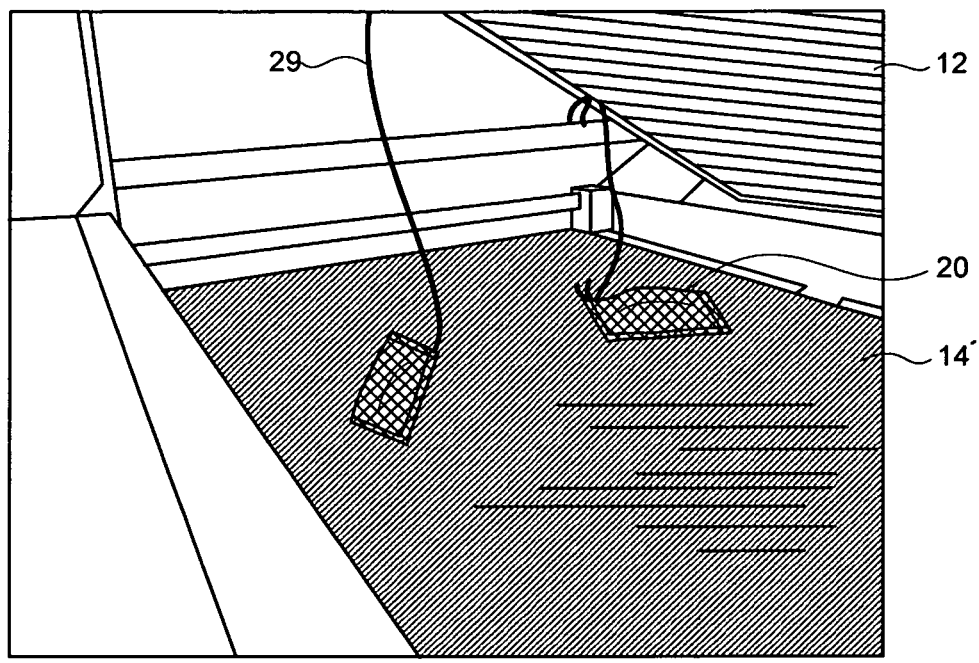
FIG. 11 illustrates an aspect of the placement of an antibacterial glass in a drain pan.

More specifically, as illustrated in FIG. 11, two pieces of the mixed antibacterial glass 20 were placed in the drain pan of an air conditioner (four-way ceiling cassette, 5 horsepower indoor unit), by binding the pieces with a string 29 to the copper tube for passing a cooling medium.

Subsequently, the air conditioner was continuously operated for 200 days in a temperature-controlled room with the temperature kept at 30° C.

After a lapse of 200 days, the occurrence of slimes in the drain water caused by microbial proliferation, and turbidity of the water were observed, and evaluated by the following criteria. The obtained results are listed in Table 1.

Good: no slime or water turbidity is found.

Fair: slime is not found, but apparent water turbidity is found.

Bad: slime and apparent water turbidity are found.

(4) Evaluation of Antibacterial Activity 2

In Example 1 and the below-described Comparative Example 1, the antibacterial activity of the mixed antibacterial glass in an air conditioner, which had been actually used in a building, was evaluated.

More specifically, in April 2009, as illustrated in FIG. 11, two pieces of the mixed antibacterial glass 20 were placed in the drain pan of an air conditioner (four-way ceiling cassette, 5 horsepower indoor unit) installed on the reception floor of a research facility which used to be a school, by binding the pieces with a string 29 to the copper tube for passing a cooling medium.

Subsequently, the air conditioner was operated in a normal manner according to the temperature in the facility. Therefore, the operation of the air conditioner was stopped when the research facility was out of operation, or when the operation of the air conditioner was not necessary.

The condition of the drain pan was photographed in November 2009, after a lapse of 7 months from the placement of the mixed antibacterial glass. The results in Example 1 and Comparative Example 1 are illustrated in FIGS. 12 and 13, respectively.

Figure 12:
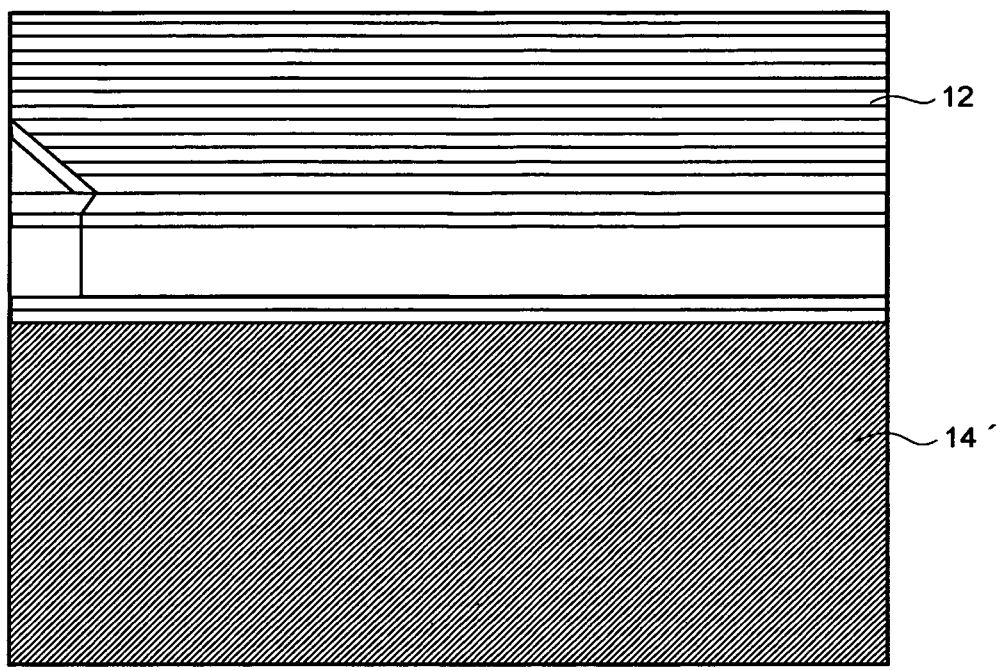
FIG. 12 illustrates the appearance in the drain pan in Example 1.

In the case of Example 1, as shown in FIG. 12, the operation of the air conditioner was stopped in November 2009 due to the mild climate, so that no drain water remained in the drain pan, and there was little evidence of slime.

Figure 13:
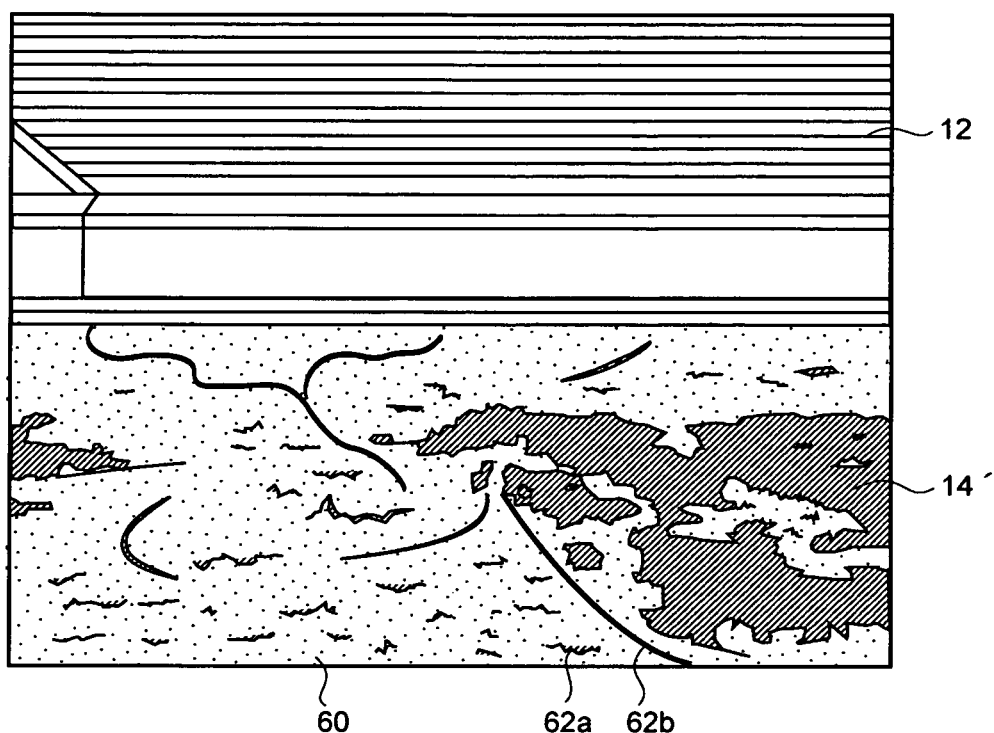
FIG. 13 illustrates the appearance in the drain pan in Comparative Example 1.

On the other hand, in the case of Comparative Example 1, as shown in FIG. 13, no drain water remained in the drain pan as was the case with Example 1, but a large amount of dry slims likely occurred during summer was found to be stuck to the bottom 14' (60).

(5) Evaluation of Drainage Safety

The safety of drainage after using the mixed antibacterial glass was evaluated.

The pH of the drain water after a lapse of 200 days under the same conditions as those for the evaluation of antibacterial activity was measured, and the evaluated by the following criteria. The obtained results are listed in Table 1.

Good: the pH of the drain water is 6 or more and 8 or less.

Fair: the pH of the drain water is 5 or more and less than 6, or more than 8 and less than 9.

Bad: the pH of the drain water is less than 5 and 9 or more.

Example 2

In Example 2, a mixed antibacterial glass was made and evaluated in the same manner as in Example 1, except that the antibacterial acidic glass was in the form of tablets having a maximum diameter of 10 mm, and 10 g of antibacterial alkaline glass, 60 g of antibacterial acidic glass, and 7 g of non-antibacterial glass were mixed. The obtained results are listed in Table 1.

Example 3

In Example 3, a mixed antibacterial glass was made and evaluated in the same manner as in Example 2, except that 20 g of antibacterial alkaline glass, 40 g of antibacterial acidic glass, 6 g of non-antibacterial glass were mixed. The obtained results are listed in Table 1.

Example 4

In Example 4, the antibacterial alkaline glass had the following composition, and in the form of crushed granules having an average particle size of 2 mm.

$SiO_2$ 46.50% by weight $Al_2O_3$ 7.50% by weight $K_2O$ 9.00% by weight $B_2O_3$ 34.00% by weight $Ag_2O$ 3.00% by weight Further, the antibacterial acidic glass was in the form of tablets having a maximum diameter of 10 mm. A mixed antibacterial glass was made and evaluated in the same manner as in Example 1, except that 10 g of antibacterial alkaline glass, 60 g of antibacterial acidic glass, and 7 g of non-antibacterial glass were mixed. The obtained results are listed in Table 1.

Example 5

In Example 5, the antibacterial acidic glass was in the form of crushed granules having an average particle size of 2 mm. A mixed antibacterial glass was made and evaluated in the same manner as in Example 4, except that 10 g of antibacterial alkaline glass, 20 g of antibacterial acidic glass, and 3 g of non-antibacterial glass were mixed. The obtained results are listed in Table 1.

Example 6

In Example 6, the antibacterial acidic glass had the following composition, and in the form of tablets having a maximum diameter of 10 mm.

$P_2O_5$ 60.27% by weight $K_2O$ 10.01% by weight $Ag_2O$ 6.00% by weight $ZnO$ 16.93% by weight $MgO$ 6.79% by weight Further, a mixed antibacterial glass was made and evaluated in the same manner as in Example 1, except that 15.3 g of antibacterial alkaline glass, 15.4 g of antibacterial acidic glass, and 3.1 g of non-antibacterial glass were mixed. The obtained results are listed in Table 1.

The weight of one piece of the antibacterial acidic glass thus obtained was 0.83 g.

Example 7

In Example 7, the antibacterial acidic glass was in the form of tablets having a maximum diameter of 6 mm. A mixed antibacterial glass was made and evaluated in the same manner as in Example 6, except that 15.2 g of antibacterial alkaline glass, 15.1 g of antibacterial acidic glass, and 3.1 g of non-antibacterial glass were mixed. The obtained results are listed in Table 1.

The weight of one piece of the antibacterial acidic glass thus obtained was 0.24 g.

Comparative Example 1

In Comparative Example 1, the antibacterial acidic glass was in the form of tablets having a maximum diameter of 10 mm. A mixed antibacterial glass was made and evaluated in the same manner as in Example 1, except that no antibacterial alkaline glass was used, and 44 g of antibacterial acidic glass and 4.4 g of non-antibacterial glass were mixed. The obtained results are listed in Table 1.

Comparative Example 2

In Comparative Example 2, a mixed antibacterial glass was made and evaluated in the same manner as in Example 1, except that no antibacterial acidic glass was used, and 40 g of antibacterial alkaline glass and 4 g of non-antibacterial glass were mixed. The obtained results are listed in Table 1.

Comparative Example 3

In Comparative Example 3, a mixed antibacterial glass was made and evaluated in the same manner as in Example 1, except that no antibacterial alkaline glass was used, and 22 g of antibacterial acidic glass and 2.2 g of non-antibacterial glass were mixed. The obtained results are listed in Table 1.

Comparative Example 4

In Comparative Example 4, a mixed antibacterial glass was made and evaluated in the same manner as in Example 1, except that the antibacterial alkaline glass had the same composition and form as those in Example 4, no antibacterial acidic glass was used, and 20 g of antibacterial alkaline glass and 2 g of non-antibacterial glass were mixed. The obtained results are listed in Table 1.

TABLE 1

| | Antibacterial alkaline glass | | | | Antibacterial acidic glass | | | | Total of anti-bacterial glasses (g) |
|---|---|---|---|---|---|---|---|---|---|
| | Standard pH (—) | standard silver ion elution amount (mg/(g·L·24 Hrs·30° C.)) | Specific surface area (cm²/g) | Compounding amount (parts by weight) | Standard pH (—) | standard silver ion elution amount (mg/(g·L·24 Hrs·30° C.)) | Specific surface area (cm²/g) | Compounding amount (parts by weight) | |
| Example 1 | 9.0 | 0.239 | 3.75 | 50 (10 g) | 5.0 | 0.074 | 10.50 | 100 (20 g) | 30 |
| Example 2 | 9.0 | 0.239 | 3.75 | 16.7 (10 g) | 6.0 | 0.025 | 3.50 | 100 (60 g) | 70 |
| Example 3 | 9.0 | 0.239 | 3.75 | 50 (20 g) | 6.0 | 0.025 | 3.50 | 100 (40 g) | 60 |
| Example 4 | 9.0 | 0.057 | 10.50 | 16.7 (10 g) | 6.0 | 0.025 | 3.50 | 100 (60 g) | 70 |
| Example 5 | 9.0 | 0.057 | 10.50 | 50 (10 g) | 5.0 | 0.074 | 10.50 | 100 (20 g) | 30 |
| Example 6 | 9.0 | 0.239 | 3.75 | 99.4 (15.3 g) | 6.0 | 0.743 | 2.92 | 100 (15.4 g) | 30.7 |
| Example 7 | 9.0 | 0.239 | 3.75 | 100.7 (15.2 g) | 6.0 | 0.966 | 3.79 | 100 (15.1 g) | 30.3 |
| Comparative Example 1 | — | — | — | 0 (0 g) | 6.0 | 0.025 | 3.50 | 100 (44 g) | 22 |
| Comparative Example 2 | 9.0 | 0.239 | 3.75 | 100 (40 g) | — | — | — | 0 (0 g) | 20 |
| Comparative Example 3 | — | — | — | 0 (0 g) | 5.0 | 0.074 | 10.50 | 100 (22 g) | 22 |
| Comparative Example 4 | 9.0 | 0.057 | 10.50 | 100 (20 g) | — | — | — | 0 (0 g) | 20 |

| | Non-antivacterial glass Compounding amount (parts by weight) | Evaluation | | | | | | | | |
|---|---|---|---|---|---|---|---|---|---|---|
| | | pH (—) | | Total silver ion elution amount* (mg/(g·L·30° C.)) | | | | | Anti-bacterial activity | drainage safety |
| | | Standard conditions | Endurance conditions | Standard conditions | Endurance conditions | pH dependence | | | | |
| | | | | | | pH 4.0 | pH 6.5 | pH 10.0 | | |
| Example 1 | 15 (3 g) | 6.0 | 7.0 | 0.160 | 0.250 | 0.123 | 0.160 | 0.246 | ○ | ○ |
| Example 2 | 11.7 (7 g) | 7.0 | 8.0 | 0.059 | 0.183 | 0.032 | 0.059 | 0.097 | ○ | ○ |
| Example 3 | 15 (6 g) | 8.0 | 8.0 | 0.066 | 0.232 | 0.021 | 0.066 | 0.101 | ○ | ○ |
| Example 4 | 11.7 (7 g) | 6.0 | 7.0 | 0.034 | 0.068 | 0.029 | 0.034 | 0.033 | Δ | ○ |
| Example 5 | 15.0 (3 g) | 6.0 | 5.0 | 0.168 | 0.274 | 0.093 | 0.168 | 0.273 | ○ | Δ |
| Example 6 | 20.1 (3.1 g) | 8.0 | 7.5 | 0.528 | 0.792 | 0.580 | 0.528 | 0.268 | ○ | ○ |
| Example 7 | 20.5 (3.1 g) | 8.0 | 7.5 | 0.672 | 1.008 | 0.704 | 0.672 | 0.342 | ○ | ○ |
| Comparative Example 1 | 10 (4.4 g) | 5.0 | 4.0 | 0.025 | 0.102 | 0.069 | 0.025 | 0.004 | X | Δ |
| Comparative Example 2 | 10 (4.0 g) | 9.0 | 9.0 | 0.239 | 0.412 | 0.038 | 0.239 | 0.170 | X | X |
| Comparative Example 3 | 10 (2.2 g) | 5.0 | 4.0 | 0.074 | 0.302 | 0.207 | 0.074 | 0.013 | X | X |
| Comparative Example 4 | 10 (2.0 g) | 8.0 | 8.5 | 0.057 | 0.370 | 0.040 | 0.057 | 0.096 | X | X |

*The total silver ion elution amount under the endurance conditions represents the total silver ion elution amount (mg/(g·L·14 days·30° C.)) for 14 days, and the other total silver ion elution amounts represent the total silver ion elution amount (mg/(g·L·24 Hrs·30° C.)) for 24 hours.

The mixed antibacterial glass of the present invention is composed of antibacterial alkaline and acidic glasses under certain conditions, and stably controls the silver ion elution amount through the interaction between these antibacterial glasses.

Consequently, the silver ion elution amount from the antibacterial glass in the drain water from an air conditioning system is stably controlled, whereby the occurrence of microorganisms in the drain water is effectively prevented.

What is claimed is:

1. A mixed antibacterial glass which achieves antibacterial effect by releasing silver ions, the mixed antibacterial glass comprising an antibacterial glass which shows alkalinity when dissolved, and another antibacterial glass which shows acidity when dissolved respectively, the silver ion elution amount from the antibacterial glass showing alkalinity being from 0.005 to 1 mg/(g·1 liter, 24 Hrs, 30° C.), wherein the silver elution amount is measured under certain conditions, the certain conditions comprising immersing 30 g of the antibacterial glass being studied in 1 liter of purified water at 30° C. and a pH of 6.5 in a closed system for 24 hours with the temperature maintained, the silver ion elution amount from the antibacterial glass showing acidity being from 0.05 to 1 mg/(g·1 liter, 24 Hrs, 30° C.) as measured under the certain conditions, the compounding amount of the antibacterial glass showing alkalinity being from 10 to 120 parts by weight with reference to 100 parts by weight of the antibacterial glass showing acidity, and the total silver ion elution amount being from 0.1 to 1 mg/(g·1 liter, 24 Hrs, 30° C.) as measured under the certain conditions, wherein the antibacterial glass showing alkalinity contains an inorganic coloring agent as a compounded component, wherein the addition amount of the inorganic coloring agent is from 0.001 to 0.5% by weight with reference to 100% by weight of the total amount of the antibacterial glass showing alkalinity;

wherein the antibacterial glass showing alkalinity is an antibacterial borosilicate glass and the antibacterial glass showing acidity is an antibacterial phosphate glass, wherein the antibacterial phosphate glass comprises 50 to 80% by weight of $P_2O_5$ with reference to 100% by weight of a total amount of the antibacterial phosphate glass;

wherein the antibacterial glass showing alkalinity and the antibacterial glass showing acidity are enclosed in a covering member having an opening for passing water.

2. The mixed antibacterial glass according to claim 1, wherein a pH measured under the certain conditions is 5 to 9, and the inorganic coloring agent is at least one compound selected from the group consisting of cobalt oxide, copper oxide, chromium oxide, nickel oxide, manganese oxide, neodymium oxide, erbium oxide and cerium oxide.

3. The mixed antibacterial glass according to claim 1, wherein the specific surface area of the antibacterial glass showing alkalinity is from 0.1 to 5 cm$^2$/g, and the specific surface area of the antibacterial glass showing acidity is from 8 to 100 cm$^2$/g.

4. The mixed antibacterial glass according to claim 1, wherein the antibacterial glass showing alkalinity is in the form of tablets having a maximum diameter of 5 to 20 mm.

5. The mixed antibacterial glass according to claim 1, wherein the antibacterial glass showing acidity is in the form of granules having an average particle size of 0.01 to 5 mm.

6. The mixed antibacterial glass according to claim 1, further comprising a non-antibacterial glass, the compounding amount of the non-antibacterial glass being from 5 to 100 parts by weight with reference to 100 parts by weight of the antibacterial glass showing acidity.

\* \* \* \* \*